United States Patent
Carson et al.

(10) Patent No.: US 6,689,864 B1
(45) Date of Patent: Feb. 10, 2004

(54) CYCLIN DEPENDENT KINASE 4 INHIBITOR

(75) Inventors: Dennis A. Carson, Del Mar, CA (US); Tsutomu Nobori, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/921,954

(22) Filed: Aug. 26, 1997

Related U.S. Application Data

(60) Continuation of application No. 08/445,648, filed on May 22, 1995, now abandoned, which is a division of application No. 08/227,800, filed on Apr. 14, 1994.

(51) Int. Cl.$^7$ .......................... C07K 1/00; C07H 21/04; A61K 38/00

(52) U.S. Cl. ........................ 530/350; 536/23.5; 514/12

(58) Field of Search ............................. 435/194, 320.1, 435/69.2; 514/2, 12; 530/350; 536/23.5

(56) References Cited

U.S. PATENT DOCUMENTS

| | | | |
|---|---|---|---|
| 4,681,840 A | * | 7/1987 | Stephenson et al. ............ 435/6 |
| 5,081,230 A | * | 1/1992 | Carney ........................ 530/387 |
| 5,149,628 A | * | 9/1992 | Croce ............................ 435/6 |
| 5,801,236 A | | 9/1998 | Kamb |
| 5,843,756 A | | 12/1998 | Stone et al. |
| 5,889,169 A | | 3/1999 | Beach et al. |
| 5,962,316 A | | 10/1999 | Beach et al. |
| 5,989,815 A | | 11/1999 | Skolnick et al. |
| 6,037,462 A | | 3/2000 | Kamb |
| 6,090,578 A | | 7/2000 | Kamb |

FOREIGN PATENT DOCUMENTS

WO     WO 93/09945 A1     5/1993

OTHER PUBLICATIONS

Ewen et al., 74 Cell 1009–1020 (1993).*
Alberts et al., Molecular Biology of the Cell, Chapter 3, pp. 95–107 (1989).*
Kamb A. et al. A cell cycle regulator potentially involved in genesis of many tumor types, Science, 1994, 264, 436–440.*
Hussussian C. et al, Germline p16 mutations in familial melanoma, Nature Genetics, 1994, 8, 15–21.*
Serrano M. et al. A new regulatory motif in cell–cycle control causing specific inhibition of cyclin D/CDK4, Nature, 1993, 366, 704–707.*
Kamb A. et al. A cell cycle regulator potentially involved in genesis of many tumor types, Science, 1994, 264, 436–440.*
Hussussian C. et al, Germline p16 mutations in familial melanoma, Nature Genetics, 1994, 8, 15–21.*
Nobori T. et al, Deletion of the cyclin–dependent kinase–4 inhibitor gene in multiple human cancers, Nature, 1994, 368, 753–756.*
ATCC Catalojue of Recombinant DNA Materials, Third Ed, 1993, Editors D.R. Moglott and WC Nierman, p. 9.*
Hayashi et al. Biochemical Biophys. Res. Comun. 202:1426–30, 1994.*
Xu et al, Cancer Research 54:5262–5264, 1994.*
Nobori et al. Cancer Research 53: 1098–1101, 1993.*
Dorland's Illustrated Medical Dictionary, 27$^{th}$ Edition, W.B. Saunders Company, p. 461, (1988).
Freeman, et al., "Clinical Trials in Gene Therapy," *Advanced Drug Delivery Reviews*, vol. 12, pp. 169–183, (1993).
Goldberg, et al., "Models of Neoplasia and Their Diagnostic Implications: A Historical Perspective," *Clinical Chemistry*, vol. 39, No. 11(B), pp. 2360–2374, (1993).
Gutierrez, et al., "Gene Therapy for Cancer," *The Lancet*, vol. 339, pp. 715–721, (Mar. 21, 1992).
Hebert, et al., "Candidate Tumor–Suppressor Genes MTS1 (p16$^{INK4A}$) and MTS2(p15$^{INK4B}$) Display Frequent Homozygous Deletions in Primary Cells From T–But Not From B–Cell Lineage Acute Lymphoblastic Leukemias," *Blood*, vol. 84, No. 12, pp. 4038–4044, (Dec. 15, 1994).
James, "Towards Gene–Inhibition Therapy: A Review of Progress and Prospects in the Field of Antiviral Antisense Nucleic Acids and Ribozymes," *Antiviral Chemistry & Chemotherapy*, vol. 2, No. 4, pp. 191–214, (1991).
Mori, et al., "Frequent Somatic Mutation of the MTS1/CDK4I (Multiple Tumor Suppressor/Cyclin–dependent Kinase 4 Inhibitor) Gene in Esophageal Squamous Cell Carcinoma[1]," *Cancer Reserach*, vol. 54, pp. 3396–3397, (Jul. 1, 1994).
Schreiber, "Tumor Immunology," *Fundamental Immunology*, Second Edition, Chapter 34, Raven Press Ltd., New York, pp. 923–955, (1989).
Talmadge, "The Pharmaceutics and Delivery of Therapeutic Polypeptides and Proteins," *Advanced Drug Delivery Reviews*, vol. 10, Elsevier Science Publishers B.V., pp. 247–299, (1993).
Tidd, "A Potential Role for Antisense Oligonucleotide Analogues in the Development of Oncogene Targeted Cancer Chemotherapy," *Anticancer Research*, vol. 10, pp. 1169–1182, (1990).
Kamb. et al., "A Cell Cycle Regulator Potentially Involved in Genesis of Many Tumor Types." *Science*, vol. 264, Apr. 15, 1994, pp. 436–440.
Nobori, et al., "Deletions of the cyclin–dependent kinase–4 inhibitor gene in multiple human cancers," *Nature*, vol. 368, Apr. 21, 1994, pp. 753–756.

(List continued on next page.)

*Primary Examiner*—Rebecca E. Prouty
*Assistant Examiner*—Malgorzata Walicka
(74) *Attorney, Agent, or Firm*—Townsend and Townsend and Crew LLP

(57) ABSTRACT

A gene that encodes an inhibitor of CDK4 has been discovered and its genomic nucleotide sequence has been identified. Susceptibility to certain cancers has been shown to be causatively related to the deletion of, or polymorphisms in, the CDK4I gene. The invention is therefore directed to the gene (CDK4I), the inhibitor protein, as well as therapeutic and diagnostic methods which utilize both the CDK4I gene and the CDK4I protein.

3 Claims, 12 Drawing Sheets

OTHER PUBLICATIONS

Tam. et al., "Differential Expression and Cell Cycle Regulation of the Cyclin–dependent Kinase 4 Inhibitor p16$^{Ink4}$," *Cancer Reserch, 54*:5816–5820, Nov. 15, 1994.

Ragione, et al., "5'–Deoxy–5'–methylthioadenosine phosphorylase and p16$^{INK4}$ deficiency in multiple tumor cell lines," *Oncogene* (1995) 10, 827–833.

Shapiro, et la., "Reciprocal Rb Inactivation and p16$^{INK4}$ Expression in Primary Lung Cancers and Cell Lines," *Cancer Research* 55, 505–509, Feb. 1, 1995.

Okuda, et al., "Frequent Deletion of p16$^{INK4a}$/MTS1 and p15$^{INK4b}$/MTS2 in Pediatric Acute Lymphoblastic Leukemia," *Blood*, vol. 85, No. 9, May 1, 1995, pp. 2321–2330.

Okamoto, et al., "Mutations and altered expression of p16$^{INK4}$ in human cancer," *Proc. Natl. Acad. Sci. USA*. vol. 91, pp. 11045–11049, Nov. 1994.

Otterson, et al., "Absence of p16$^{INK4}$ protein is restricted to the subset of lung cancer lines that retain wildtype RB." *Oncogene* (1994) 9, 3375–3378.

Igaki, et al., "Highly Frequent Homozygous deletion of the p16 Gene in Esophageal Cancer Cell Lines," *Biochemical and Biophysical Res. Comm.*, vol. 203, No. 2, Sep. 15, 1994, pp. 1090–1095.

Kundson, "Mutation and Cancer: Statistical Study of Retinoblastoma," *Proc. Natl. Acad. Sci. USA*, vol. 68, No. 4, pp. 820–823, Apr. 1971.

A new regulatory motif in cell–cycle control causing specific inhibition of cyclin D/CDK4 Serrano, et al., *Nature, 366*:704–707, Dec. 16, 1993.

Allele–specific enzymatic amplification of β–globin genomic DNA for diagnosis of sickle cell anemia Wu, et al., *Proc. Natl. Acad. Sci. USA, 86*:2757–2760, 4/89.

δ–Aminolevulinate Dephydratase Deficient Porphyria: Identification of the Molecular Lesions in a Severely Affected Homozygote Plewinska, et al., *Am. J. Hum Genet., 49*:167–174, 1991.

Detection of polymorphisms of human DNA be gel electrophoresis as single–strand conformation polymorphisms Orita, et al., *Proc. Natl. Acad. Sci USA, 86*:2766–2770, 4/89.

How Cells Cycle Toward Cancer Jean Marx, *Science, 263*:319–321, Jan. 21, 1994.

Absence of Methylthioadenosine Phosphorylase in Human Gliomas Nobori, et al., *Cancer Reserach, 51*:3193–3197, Jun. 15, 1991.

Methylthioadenosine Phosphorylase Deficiency in Human Non–Small Cell Lung Cancers Nobori, et al., *Cancer Research, 53*:1098–1101, Mar. 1, 1993.

Selective killing of human malignant cell lines deficient in methylthioadenosine phosphorylase, a purine metabolic enzyme Kamatani, et al., *Proc. Natl. Acad. Sci. USA*, No. 2, 78:1219–1223, 2/81.

Methylthioadenosine Phosphorylase Deficiency in Human Leukemias and Solid Tumors Fitchen, et al., *Cancer Research, 46*:5409–5412, 10/86.

Deficiency of 5' deixt–5'–methylthioadenosine phosphorylase activity in malignancy Della Ragione, et al., *Biochem. J, 281*:533–538, 1992.

* cited by examiner

FIG. 2a

```
   1  TTTGGGGNNA AGTTTGGGAA AANCCAATCC TCCTTCCTTT CCAACNNTGC
  51  TTCTGGCGAG GCTCCTTCCC GGCTTGTTCC CCCNGGGGGA AGACCCAACC
 101  TGGGCCGACC TTCAGGGTTC CCACATTCCC TAANTGCTCG GAGTTAATAN
 151  CACCTCCTCC GAGNACTCGC TCACGNCGTC CCCTTNCCTG GAAAGATACC
 201  GCGNTCCCTC NAGAGGATTT GAGGGACAGG GTCGGAGGGG NCTCTTCCGC
 251  CAGCACCGGA GGAAGAAAGA GGAGGGGCTG GCTGGTCACC AGAGGGTGGG
 301  GCGGACCGCG TGCGCTCGGC GTCTGCGGAG AGGGGGAGAG CAGGCAGCGG
 351  GCGGCGGGGA GCAGCATGGA GCCGGCGGCG GGGAGCAGCA TGGAGCCTTC
 401  GGCTGACTGG CTGGCCACGG CCGCGGCCCG GGGTCGGGTA GAGGAGGTGC
 451  GGGCGCTGCT GGAGGCGGGG GCGCTGCCCA ACGCACCGAA TAGTTACGGT
 501  CGGAGGCCGA TCCAGGTGGG TAGAGGGTCT GCAGCGGGAG CAGGGGATGG
 551  CGGGCGACTC TGGAGGACGA AGTTTGCAGG GGAATTGGAA TCAGGTAGCG
 601  CTTCGATTCT CCGGAAAAAG GGGAGGCTTC CTGGGGAGTT TTCAGAAGGG
 651  GTTTGTAATC ACAGACCTCC TCCTGGCGAC GCCCTGGGGG CTTGGGAAGC
 701  CAAGGAAGAG GAATNAGGAG CCACGCGCGT ACAGATCTCT CGAATGCTGA
 751  SAMGATYTTR AGGGSSGRAM ATATTTGTAT TCAGATGGAA GTATKCTCTT
 801  TATCAGATAC AAAATTTACG AACGTTTGGG ATAAAAGGG AGTCTTAAAG
 851  AAATKTAAGA TGTKCTGGGA CTACTTAGCC TCCAATTCAC AGATACCTGG
 901  ATGGAGCTTA TCTTTCTTAC TAGGAGGGAT TATCAGTGGA AATCTGTGGN
 951  GTATGTTGGA ATAAATATCG AATATAAATT TTGATCGAAA TTATTCAGAA
1001  GCGGCCGGGC GCGGTGCCTC ACGCCTTGTA ATCCCTTCAC TTTGGGAGAT
1051  CAAGGCGGGG GGGAATCANC TGAGGTCGGG AGTTCGAGAA CAGCCTGGGC
1101  AACAGGTGAA AACCTCGCCT CCTACTAAAA AATACAAAAA GTAGNC
```

FIG. 2b(1)

```
   1 GAATTCATTG TGTACTGAAG AATGGATAGA GAACTCAAGA AGGAAATTGG
  51 AAACTGGAAG CAAATGTAGG GGTAATTAGA CACCTGGGGC TTGTGTGGGG
 101 GTCTGCTTGG CGGTGAGGGG GCTCTACACA AGCTTCCTTT CCGTCATGCC
 151 GGCCCCCACC CTGGCTCTGA CCATTCTGTT CTCTCTGGCA GGTCATGATG
 201 ATGGGCAGCG CCCGAGTGGC GGAGCTGCTG CTGCTCCACG GCGCGGAGCC
 251 CAACTGTGCC GACCCCGNCA CTCTCACCCG ACCCGTGCAC GACGCTGCCC
 301 GGGAGGGCTT CCTGGACACG CTGGTGGTGC TGCACCGGGC CGGGGCGCGG
 351 CTGGACGTGC GCGATGCCTG GGCCGTCTG CCCGTGGACC TGGCTGAGGA
 401 GCTGGGCCAT CGNGATGTCG CACGGTACCT GCGCGCGGCT GCGGGGGGCA
 451 CCAGAGGCAG TAACCATNCC CGNATAGATG CCGCGGAAGG TCCCTCAGGT
 501 GAGGACTGAT GATCTNAGAA TTTGNCCCCT GAGAGCTTCC AAAGCTCAGA
 551 GNATTCATTT TCCAGCACAG AAAGTNCAGC CCGGGAGANC AGTCTCCGGT
 601 CTTGTCTCAG CTCACGCGCC AATCGGTGGG ACGGCCTGAG TCTCCCTATC
 651 GCCCTGCCCC GCCAGGGCGG CAAATGGGAA ATAATCCCGA AATGGACTTG
 701 CGCACGTGAA AGCCCATTTT GTACATTATA CTTCCCAAAG CATACCACCA
 751 CCCAAACACC TACCCTCTGC TAGTTCAAGG CCTAGACTGC GGAGCAATGA
 801 AGACTCAAGA GGCTAGAGGT CTAGTGCCCC CTCTTCCTCC AAACTAGGGC
 851 CAGTTGCATC CACTTACCAG GTCTGTTTCC TCATTTGCAT ACCAAGCTGG
 901 CTGGACCAAC CTCAGGATTT CCAAACCCAA TTGTGCGTGG CATCATCTGG
 951 AGATCTCTCG ATCTCGGCTC TTCTGCACAA CTCAACTAAT CTGAACCTCC
1001 TCAGCTAATC TGACCCTCCG CTTNATGCGG TAGAGTTTAC CAGAGCTGCC
```

FIG. 2b(2)

```
1051  CCAGGGGGTT CTGGGGACAT CAGGACCAAG ACTTCGCTGA CCCTGGCAGT
1101  CTGTGCACCG GAGTTGGCTC CTTTCCCTCT TAAACTTGTG CAAGAGATCG
1151  CTGAGAGATG AAGGTAGAAT TATGGTCCTC CTTGCCCTNG CCTTTCCTTT
1201  TAGTGATCTC AAAGCATCCT CCCTCCGTCC CCATTCCATG GCCCCAGTTC
1251  ACTACTCCCA CAGCTGTCTG GTGAAACTGA CAACATTACT CAATTGTTTC
1301  TGGGGGGAGG AACATTTTTT TTTGAAACAA AATAGATATA TGAAACAGTA
1351  CACGGGAATT AACACGATTA TTTAAGGTAA AACATGACCT TGAAGATTAT
1401  GAAATCCATC TTATTTTGGC CCAGAACGGG GGCATTGGKC TCCTTGGCCC
1451  ATAGGGGAGC TGGGGAGGAC AGGGTGAAGA GTTAGCTCTA AGCCCTCTNN
1501  TTGGAGATGC TGTAAATACA GAACGCAAAA TCACCTTCGA AGTTAAAGAC
1551  GCGAAGTTCT TCTTTACTCG GCCCCTCCTC CCCTCCCCCC CGACAATTCC
1601  CTCCAGTTAC AGCTAGCATC CAGGTCCCGG GAGGTGAAGA AGGAGACTTC
1651  GGCTCCAGTT ACAGCTAGCA TCCGGGTCCC GATTTAGAAG GAGCTGCCAA
1701  TTACAGCGCG GTTCCAGGGC TGAGCAAAAA GCCTGAGGAG CCAAGTGGGA
1751  GAGGGAGTAA AACTACTGAA TTGGGCCACA AGCAAATGAA TAAACTGAAC
1801  GACTCTTAAC CAAACCTAAT ATATTTAATC CAAACACACA AGTCTTTCAT
1851  TTCTTCCCTC CTCCCTTCCT TCTCTTACTC CCCAACACCC CCTCTTCAAG
1901  CACAATTAAT TATATGGTTA GATTCTACTG CGTGATCAGC CCTGTTCTAG
1951  GTGGTGGGCA CGCCAAGGTG AATGAGACCA AACAAGAGTC TTGCCCTCAT
2001  GGGGTTTACA TTTGGAGACA GAGTCGATCT GTTGCCCAAC CTGGAGTGCA
2051  GTGGCGCGAT CACAGCTCAC TGCAGCCTCA AACTCCCTGG CTCAAGGGGT
2101  TCTCCCACCT GAGCCTCCCG ACTAGCTGGG ACCACAGGTG CACGCCACGA
2151  CGCCTGGGTT TGTTTGTTTG TTTAATAGAG ACGAAGGTCT CACCATGTTA
```

FIG. 2b(3)

```
2201  TCTGGGCTCA AGCGATCATC CCCCCTCCTC CTCCTAAAGT ACTGGGATTA
2251  CAGTCCCAAG CTATCTTGCC CGACCTGGGA AACAGACGTT AAGGAAGATA
2301  ACAATCTATT TTCAGAGAGC GAGTTTATAA AACCAATGCA ATGGGTAAAT
2351  ATGAAGTGTG AATAGGAGGA GAAGCTAAAG AGTGGTCGGA GAATCTAATG
2401  CAAGCTACGG GAGAAAGAAA CTCAAGTGCA AATGCTGCCT CAGGAATAAA
2451  CGTAAAAAGA GACTTTCAAG TGCAAATGCT CCCTCAGGAA TAAAATAATC
2501  TTGAGACTCT CAAGTGTAAA TGCTGCCTCG GGAGAACCGA ACGGCGAGCT
2551  GGAGCCCATA CGCAACGAGA TTAGAGAGGA AGGCAGAAGC CAGAGCACAT
2601  GAATAAATGA GCATCCATTT TGTTTCAGAA ATGATCGGAA ACCATTTGTG
2651  GGTTTGTAGA AGCAGGCATG CGTAGGGAAG CTACGGGATT CCGCCGAGGA
2701  GCGCCAGAGC CTGAGGCGCC CTTTGGTTAT CGCAAGCTGG CTGGCTCACT
2751  CCGCACCAGG TGCAAAAGAT GCCTGGGGAT GCGGGAAGGG AAAGGCCACA
2801  TCTTCACGCC TTCGCGCCTG GCATTGTGAG CAACCACTGA GACTCATTAT
2851  ATAACACTCG TTTTCTTCTT GCAACCCTGC GGGCCGCGCG GTCGCGCTTT
2901  CTCTGCCCTC CGCCGGGTGG ACCTGGAGCG CTTGAGCGGT CGGCGCGCCT
2951  GGAGCAGCCA GGCGGGCAGT GGACTAGCTG CTGGACCAGG GAGGTGTGGG
3001  AGAGCGGTGG CGGCGGGTAC ATGCACGTGA AGCCATTGCG AGAACTTTAT
3051  CCATAAGTAT TTCAATGCCG GTAGGGACGG CAAGAGAGGA GGGCGGGATG
3101  TTCCACACAT CTTTGACCTC AGGTTTCTAA CGCCTGTTTT CTTTCTGCCC
3151  TCTGCAGACA TCCCCGATTG AAAGAACCAG AGAGGCTCTG AGAAACCTCC
3201  GGAAACTTAG ATCATCAGTC ACCGAAGGTC CTACAGGGCC ACAACTGCCC
3251  CCGCCACAAC CCACCCCGCT TTCGTAGTTT TCATTTAGAA AATAGAGCTT
3301  TTAAAAATGT CCTGCCTTTT AACGTAGATA TATGCCTTCC CCCACTACCG
```

FIG. 2b(4)

```
3351  TAAATGTCCA TTTATATCAT TTTTTATATA TTCTTATAAA AATGTAAAAA
3401  AGAAAAACAC CGCTTCTGCC TTTTCACTGT GTTGGAGTTT TCTGGAGTGA
3451  GCACTCACGC CCTAAGCGCA CATTCATGTG GGCATTTCTT GCGAGCCTCG
3501  CAGCCTCCGG AAGCTGTCGA CTTCATGACA AGCATTTTGT GAACTAGGGA
3551  AGCTCAGGGG GGTTACTGGC TTCTCTTGAG TCACACTGCT AGCAAATGGC
3601  AGAACCAAAG CTCAAATAAA AATAAAATAA TTTTCATTCA TTCACTCATT
3651  TATTGTCAAC ATTTATTGAG CACCTATTAC AACAATTTCA TCGCATGGAA
3701  GACAGCATCG TTTCTGACAC TGTTGTTTCA TGTATCTCTT AGAAAAACGC
3751  TGCTATTAGA CATCTAACAC TATTTATCTT GAGGTGATAA AATATCAAAA
3801  GCCGTGTCTC AAGATCGATG AAATGCGGTT AAAATGATGA ATAGAAACTC
3851  TAGGGGGACC TCATATCGAT AGACTCGAGA CTGGCACATC TGGAGATCCG
3901  TATTTATCCG GCTTCCCCTT CCAGATCACG CGAGGTTTGG GATATTTTGC
3951  TCACCAGGCC TCAGCCAGGT AACTGAATCC AGCCAACCCT GGCCCATAGT
4001  CTCGGAATCC GACTCGGCTC CCAGTCCCCG CCTCGGCGTT CTGAGACCCC
4051  CAGGCTGGGT TCCAAGAGGG CTGTGAGGTT GCGAATGACT GCTGCCAAAC
4101  CGGAAGGAAC TCTGCGGTTC TCTGCCACAG TGGGATTGTT GCAGGCACGC
4151  GGCTCAGACT TCACTGAGGT TGGGAGATGC TCCTGTCCAC GCTGCCTCAT
4201  CCCGTGCTGG AGCACTGCAC CTCTATTTTT TTTTTTAGGG TACACGCCAC
4251  ATAACATAAA ACTAAAAATT TTAAAGAGTA GAATTC
```

FIG. 3

```
  5 CGGCACGAGGCAGCATGGAGCCTTCGGCTGACTGGCTGGCCACGGCCGCG  54
    ||||   | ||||||||||||||||||||||||||||||||||||||||
376 CGGCGGGGAGCAGCATGGAGCCTTCGGCTGACTGGCTGGCCACGGCCGCG 425

55 GCCCGGGGTCGGGTAGAGGAGGTGCGGGCGCTGCTGGAGGCGGTGGCGCT 104
    |||||||||||||||||||||||||||||||||||||||||| ||||||
426 GCCCGGGGTCGGGTAGAGGAGGTGCGGGCGCTGCTGGAGGCGGGGGCGCT 475

105 GCCCAACGCACCGAATAGTTACGGTCGGAGGCCGATCCAGGT 146
    |||||||||||||||||||||||||||||||||||||||||
476 GCCCAACGCACCGAATAGTTACGGTCGGAGGCCGATCCAGGT 517
```

FIG. 4a

```
189 CAGGTCATGATGATGGGCAGCGCCCGAGTGGCGGAGCTGCTGCTGCTCCA 238
    ||||||||||||||||||||||||||||||||||||||||||||||||||
142 CAGGTCATGATGATGGGCAGCGCCCGAGTGGCGGAGCTGCTGCTGCTCCA 191

239 CGGCGCGGAGCCCAACTGTGNCGACCCCGNCACTCTCACCCGACCCGTGC 288
    |||||||||||||||| |:||||||||:||||||||||||||||||||||
192 CGGCGCGGAGCCCAACTGCGCCGACCCCGCCACTCTCACCCGACCCGTGC 241

289 ACGACGCTGCCCGGGAGGGCTTCCTGGACACGCTGGTGGTGCTGNANCGG 338
    |||||||||||||||||||||||||||||||||||||||||||:|:|||
242 ACGACGCTGCCCGGGAGGGCTTCCTGGACACGCTGGTGGTGCTGCACCGG 291

339 GCGGGGCGCGGGTGGACGTNCGCGAATNCCTGGGGNCGTCTTTCCGTNG 388
    ||||||||||| |||||||:|||| ||:|||||||:||||   ||||:|
292 GCCGGGGCGCGGCTGGACGTGCGCG.ATGCCTGGGGCCGTCTGCCCGTGG 340

389 ACCTGGNTTNANGAGCTTGGNCATCGNGAATNTCGNACGGTACCTNCCCG 438
    ||||||: |:|:||||  ||:|||||:| ||:|||:|||||||||:  ||
341 ACCTGGC.TGAGGAGCTGGGCCATCGCG.ATGTCGCACGGTACCTGCGCG 388

439 CNGTTNGGGGGG...ACANAGGNAGGAACNATNCCC 472
    |:| |: ||||||   ||:|||:|| |||:||:|||
389 CGGCTGCGGGGGGCACCAGAGGCAGTAACCATGCCC 424
```

FIG. 6

```
 18 GATGATGGGCAGCGCCTGAGTGGCGGAGCTGCTGCTGCTCCACGGCGCGG  67
    ||||||||||||||| |||||||||||||||||||||||||||||||||
150 GATGATGGGCAGCGCCCGAGTGGCGGAGCTGCTGCTGCTCCACGGCGCGG 199

68 AGCCCAAC  75
    ||||||||
200 AGCCCAAC 207
```

FIG. 7

```
404 AATTCGGCACGAGGCAGCATGGAGCCTTCGGCTGACTGGCTGGCCACGGC 453
    ||||||||||||||||||||||||||||||||||||||||||||||||||
  1 AATTCGGCACGAGGCAGCATGGAGCCTTCGGCTGACTGGCTGGCCACGGC  50

454 CGCGGCCCGGGGTCGGGTAGAGGAGGTGCG................GG 485
    |||||||||||||||||||||||||||||||                ||
 51 CGCGGCCCGGGGTCGGGTAGAGGAGGTGCGGGCGCTGCTGGAGGCGGTGG 100

486 CGCTGCCCAACGCACCGAATAGTTACGGTCGGAGGC 521
    ||||||||||||||||||||||||||||||||||||
101 CGCTGCCCAACGCACCGAATAGTTACGGTCGGAGGC 136
```

FIG. 10

```
   1 TTTATACAGA GCATGACAGT GGGGTCCTCA CTAGGGTCTG TCTGCCACTC
  51 TACATATTTG AAACAGGAGT GGCTTCTCAG AATCCAGTGA ACCTAAATTT
 101 TAGTTTTAGT TGCTCACTGG ACTGGGTTCT AGGAGACCCC CTGTGTTAGT
 151 CTGTGGTCAT TGCTAGSAGA ATCACTTAAT TTTTTCTAGA CTCTAGGAGA
 201 AAACAGTTGG TGGTGTACTC ATCACGGGTT AACAATTTCT TCTCTCCTTC
 251 CATAGGCATG GAAGGCAGCA CACCATCATG CCTTCAAAGG TCAACTACCA
 301 GGCGAACATC TGGGCTTTGA AGGAAGAGGG CTGTACACAT GTCATAGTGA
 351 CCACAGCTTG TGGCTCCTTG AGGGAGGAGA TTCAGCCCGG CGATATTGTC
 401 ATTATTGATC AGTTCATTGA CANNNNNNNN NNNNNNNNNN GAGGTCGACG
 451 GTATCGATAA GCTTTGTAAA CAATTGTCTT TAGCTTATCC AGAGGAATTG
 501 AGTCTGGAGT AAAGACCCAA ATATTGACCT AGATAAAGTT GACTCACCAG
 551 CCCTCGGAGG ATGGAAAGAT GGCCTTAAAA TAAAACAAAC AAAAACCTTT
 601 TTTGCTTTAT TTTGTAGGAC CACTATGAGA CCTCAGTCCT TCTATGATGG
 651 AAGTCATTCT TGTGCCAGAG GAGTGTGCCA TATTCCAATG GCTGAGCCGT
 701 TTTGCCCCAA AACGAGAGAG GTGTGTAGTC TTTCTGGAAG GTGTACCAGA
 751 ATAAATCATG TGGGCTTGGG GTGGCATCTG GCATTTGGTT AATTGGCAGA
 801 CGGAGTGGCC CCATACCCTC ACTCAAGTTT GCTTTGTATT ATGCAAGTTT
 851 ATGGAGAGTT ATTTCCTGTT GCTAATAATT TNNNNNNNNN NNNNNNNNNN
 901 AAGTGCAGCC TTAAGTTGTG CATGTGCTAG TATGTTTTGA AGTTTCTGGT
 951 TTTTCTTTTC TAGGTTCTTA TAGAGACTGC TAAGAAGCTA GGACTCCGGT
1001 GCCACTCAAA GGGGACAATG GTCACAATCG AGGGACCTCG TTTTAGCTCC
1051 CGGGCAGAAA GCTTCATGTT CCGCACCTGG GGGGCGGATG TTATCAACAT
1101 GACCACAGTT CCAGAGGTGG TTCTTGCTAA GGAGGCTGGA ATTTGTTACG
1151 CAAGTATCGC CATGGGCACA GATTATGACT GCTGGAAGGA GCACGAGGAA
1201 GCAGTAGGTG GAATTCTTTT CTAAGCACAT ATAGCATGGG TTTCTGGGTG
1251 CCAATAGGGT GTCTTAACTG TTTGTTTCTA TTACGTTAGT TTCAGAAAGT
1301 GCCTTTCTAC AAGGTTTTGA AGTTGTTAAT ATTTTCTGTA GTTCCATTGG
1351 AAGGTAAGAA CAAAGATCAA AAGAAAGAAA GAGACACTTT TACCCAAGGA
1401 TCAGTAGTGA AAATAGTACA TTGTAGGCAT GTAGATGTGT TGAGAATCAT
```

CYCLIN DEPENDENT KINASE 4 INHIBITOR

This is a continuation of application Ser. No. 08/445,648, filed May 22, 1995 (now abandoned), which was a divisional application of Ser. No. 08/227,800 filed Apr. 14, 1994.

BACKGROUND OF THE INVENTION

1. Field of the Invention.

The invention relates to the detection of genetic abnormalities that confer susceptibility to certain cancers in humans. More specifically, the invention relates to methods for detecting deletions of, or polymorphisms in, a newly discovered gene which encodes a tumor suppressor.

2. History of the Prior Art.

In recent years, a growing body of evidence has developed which supports the theory that the development of certain tumors is suppressed by gene products ("tumor suppressors") which inhibit cellular proliferation (see e.g., the review in Marx, Science, 263:319–320, 1994). Conversely, if the tumor suppressors which would ordinarily be present in a cell are either absent (due, for example, to a gene deletion) or less active (due, for example, to a gene mutation), tumor growth which would otherwise be inhibited may go unchecked. However, although the growth of certain tumors has been positively demonstrated to relate to the deletion of a tumor suppressor expressing gene, it has not yet been shown that mutations in the same genes will allow abnormal cellular proliferation to occur.

The growth cycle of eukaryotic cells is regulated by a family of protein kinases known as the cyclin-dependent kinases ("CDK's"). As shown in FIG. 1, the cyclins and their associated CDK's move cells through the three phases of the growth cycle ($G_1$, S and $G_2$, respectively) leading to division in the mitosis phase (M). The cyclin/CDK complexes whose role in cellular proliferation has been most clearly defined to date are the cyclin D/CDK enzymes, which are believed to assist in the progression of the $G_1$ growth cycle phase. Of these enzymes, cyclin D1 is believed to be an oncogene, whose overexpression stimulates excessive cell division through the continuous production of kinase, thus contributing to the development of cancers of, for example, the breast and esophagus. Cyclin D1 is specifically bound by CDK4 as part of a multiprotein complex that also consists of a protein known as p21 and cell nuclear antigen.

Known inhibitors of such cyclin/CDK overexpression include the tumor suppressor protein p53 and the protein product of the retinoblastoma (Rb) gene. Recently, another putative inhibitor (p16) was isolated and a cDNA for the inhibitor was partially sequenced by Serrano, et al, *Nature*, 366:704–710, 1993. The authors demonstrated that p16 binds CDK4 to inhibit the activity of the CDK4/cyclin D enzymes. Based on data indicating that p16 prevented phosphorylation by CDK/cyclin D of certain Rb growth cycle proteins, the authors proposed that p16 acts in vivo upstream and downstream of Rb to form a negative feedback loop to regulate cellular proliferation. However, no connection between p16 and the occurrence or inhibition of particular cancers was suggested, nor has any information been published concerning the genomic structure of the gene encodings p16.

SUMMARY OF THE INVENTION

Prior to the publication of the Serrano, et al., article referred to above, the inventors discovered a tumor suppressor gene (hereafter, "CDK4I") and identified its genomic structure (see, SEQ ID NO's: 1–2). In non-malignant cells, CDK4I maps to chromosome 9p21 and is physically adjacent to the gene for methylthioadenosine phosphorylase (MTAse) (see, FIG. 4(b)). MTAse deficiencies resulting from deletions of, or mutations in, the gene for MTAse have been shown to be directly related to the onset of certain cancers (see, Nobori, et al, *Cancer Res*. 53:1098–1101, 1993, the disclosure of which are incorporated herein for reference regarding the role of MTAse in cancer development, and SEQ ID NO: 14, the nucleotide sequence of genomic MTAse).

Approximately one-half of all tumor cells which have been identified to date as either lacking CDK4I or containing mutations or rearrangements (collectively, "polymorphisms") of the CDK4I gene also lack MTAse. The inventors have also identified mutations in the CDK4I gene which are present in the tumor cells of patients with certain cancers. The invention is therefore directed to methods to detect (a) deletions of the CDK4I gene in cells, and (b) polymorphisms, which deletions and polymorphisms are indicative of susceptibility to certain cancers.

More specifically, in one aspect, the invention comprises methods for detecting point mutations in, or deletions of, the CDK4I gene. Such methods include polymerase chain reaction (PCR) based assays, gel electrophoresis of single-strand conformation polymorphisms, direct sequencing, and restriction endonuclease digestion. Detection of a deletion of the CDK4I gene will preferably be performed by a unique competitive PCR technique.

In another aspect, the invention comprises methods for detection of CDK4I proteins and biologically active fragments thereof (collectively, "CDK4I") in a biological cell sample.

In another aspect, the invention comprises screening protocols for susceptibility to particular cancers based on detection of polymorphisms associated with the occurrence of the cancers.

In another aspect, the invention comprises screening protocols for susceptibility to particular cancers based on detection of polymorphisms in, or deletions of, the genes for both CDK4I and MTAse, as well as detection of deficiencies in the products of the genes.

In another aspect, the invention comprises genomic CDK4I, expression products of the CDK4I gene, CDK4I and fragments thereof, as well as antibodies which will specifically bind CDK4I gene expression products, CDK4I and CDK4I fragments.

BRIEF DESCRIPTION OF THE DRAWINGS

FIGS. 2 (a–b) depicts the full-length genomic sequence (SEQ ID NOS:1 and 2) for the human CDK4I gene, wherein the exons CDK4I5' (SEQ ID NO:3), CDK4I' (SEQ ID NO:4) and CDK4I3' (SEQ ID NO:5) are underlined.

FIG. 3 compares the 5' regions of the genomic DNA sequence shown in FIG. 2 (bottom line; SEQ ID NO:16) with the cDNA sequence reported by Serrano, et al., in *Nature*, 366:704–710, 1993 (top line; SEQ ID NO:15), wherein differences are indicated by the absence of a vertical line between the sequences.

FIG. (b) shows the relationship of the region to the MTAse and INF-α genes on chromosome 9.

Figure 5:
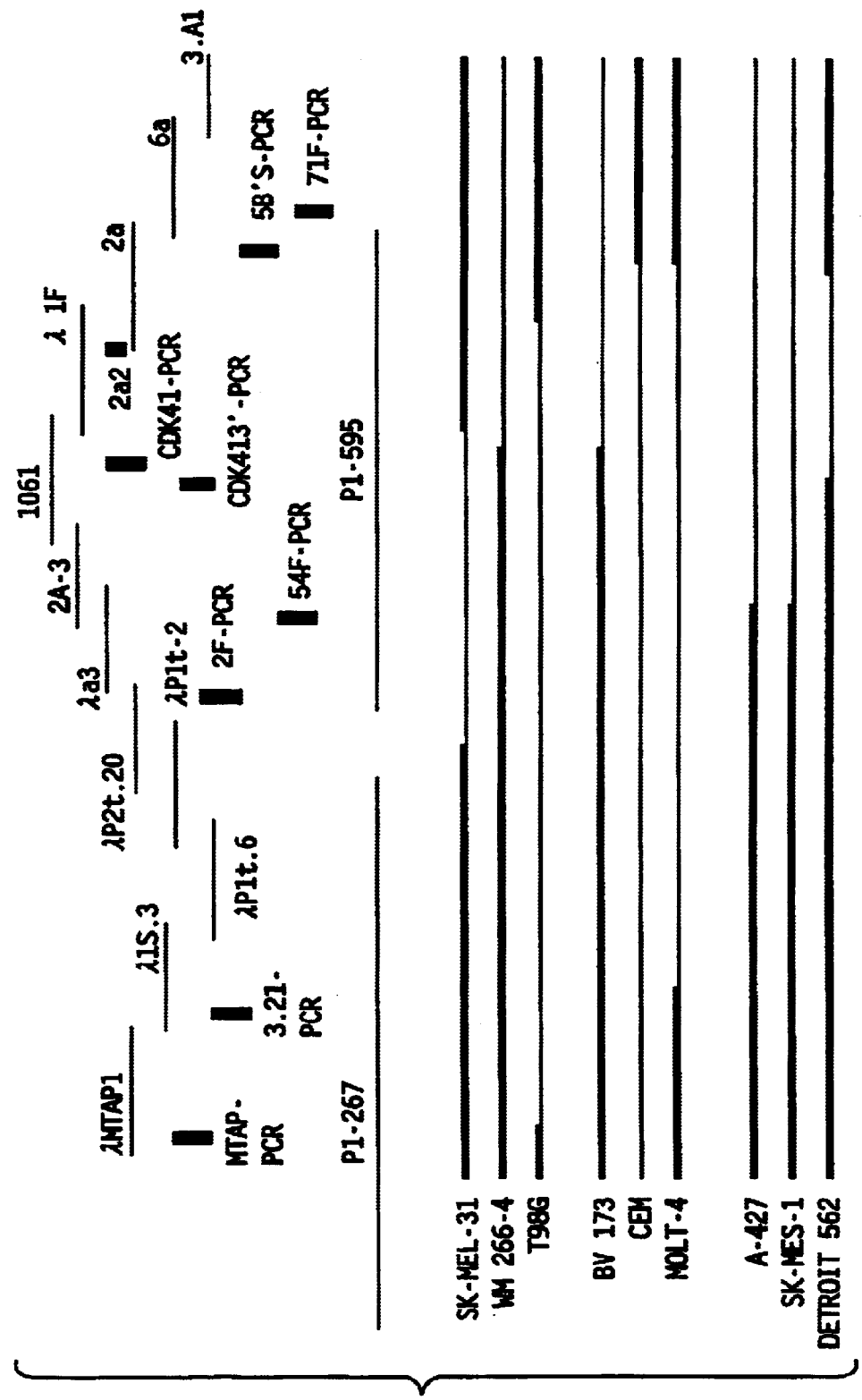

FIG. 5 maps sites of deletions between the 54F and 5BS regions of the region between the gene loci for MTAse and INF-a, wherein the site of the gene for CDK4I is in the most frequently deleted region.

FIG. 6 compares the normal DNA sequence of the CDK4I gene (bottom line; SEQ ID NO:20) and a mutated sequence of the gene (top line; SEQ ID NO:19) containing a single base substitution found in cells from a human patient with familial melanoma.

FIG. 7 compares the normal DNA sequence of the CDK4I gene (bottom line; SEQ ID NO:22) and a mutated sequence of the gene (top line; SEQ ID NO:21) containing an intragenic microdeletion found in a leukemia cell line.

Figure 8:
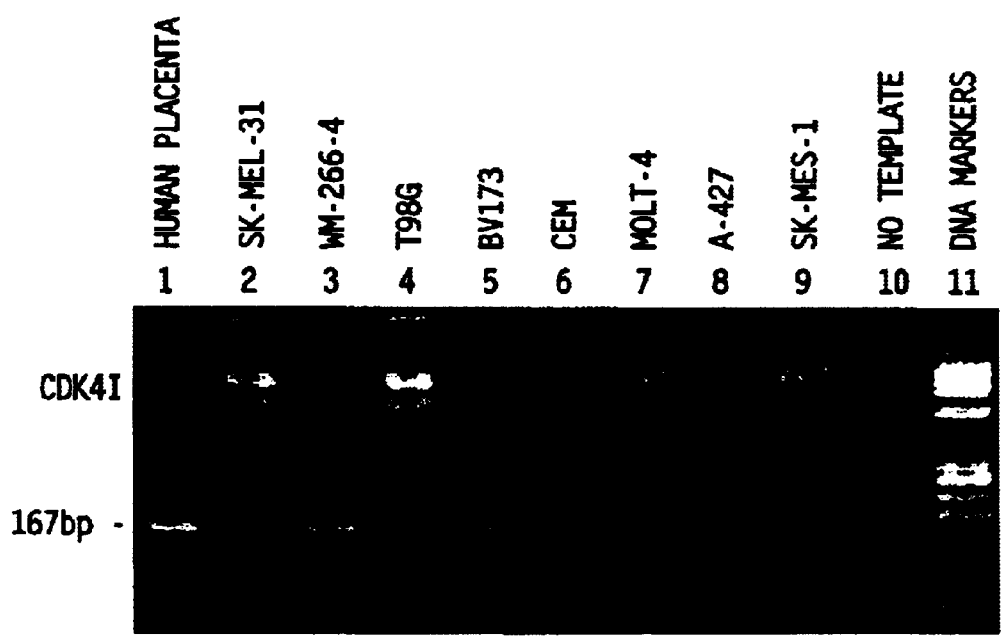

FIG. 8 depicts the results of PCR-based assays for the CDK4I gene in several human malignant cell lines. Lane1= placental cells, lane 2=SK-MEL-31 (ATCC HTB73; a melanoma cell line); lane 3=WM 266–4 (ATCC CRL 1676; a melanoma cell line), lane 4=T98G (a glioma cell line), lane 5=BV173, lane 6=CEM (ATCC CCL 119; a lymphoblastic leukemia cell line), lane 7=MOLT-4 (ATCC 1582; a lymphoblastic leukemia), lane 8=A549 (ATCC CCL 185; a non-small cell lung cancer cell line), lane 9=SK-MES-1 (ATCC HTB 58; a non-small cell lung cancer cell line). Lane 10 has no templates and lane 11 has DNA markers.

Figure 9:
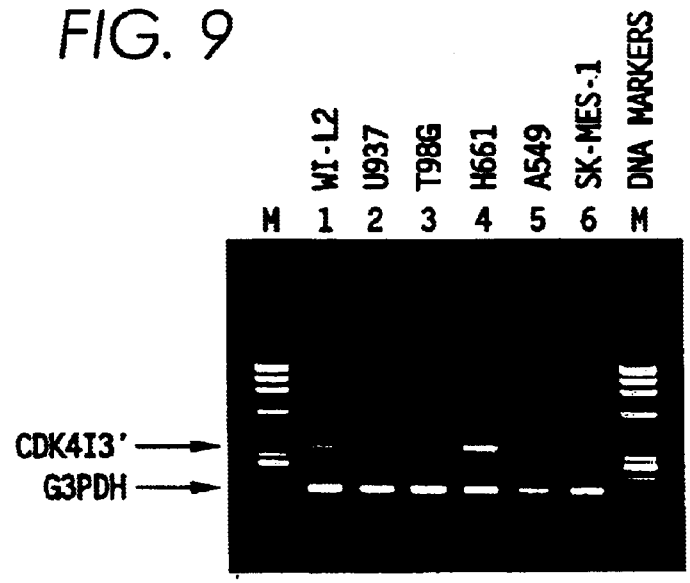

FIG. 9 depicts the results of reverse transcriptase PCR-based assays for mRNA corresponding to the CDK4I gene in several malignant cell lines. Lane 1=WIL2-NS (ATCC CRL 8155; a normal lymphoblastoid cell line), lane 2=U937 (ATCC CRL 1593; a leukemia cell line ), lane 3=T98G (ATCC CRL 1690; a glioma cell line), lane 4=H661 (ATCC HTB-183; a non-small cell lung cancer cell line), lane 5=A-549 (ATCC CCL 185; a non-small cell lung cancer cell line), and lane 6=SK-MES-1 (ATCC HTB 58; a non-small cell lung cancer cell line). M=DNA markers.

FIG. 10 is the genomic nucleotide sequence for MTAse (SEQ ID NO:23), with the exons underlined.

DETAILED DESCRIPTION OF THE INVENTION

I. IDENTIFICATION AND CHARACTERIZATION OF GENOMIC CDK4I

In the Sequence Listing appended hereto, the full-length genomic nucleotide sequence for the human CDK4I gene (i.e., "CDK4I polynucleotide") is set forth at SEQ ID NO's: 1 and 2 (and is reproduced in FIGS. 2 (a–b)). SEQ ID NO'S 3–5 contain the nucleotide sequences for the CDK4I gene exons; these exons are underlined in FIGS. 2 (a–b), thus showing the boundaries between the exons (hereafter, "CDK4I'", "CDK4I3'" and "CDK4I5'") as well as introns of the gene. The CDK4I' exon contains a palindromic region of 4 inverted repeats which likely contribute to the structural stability of the expressed CDK4I protein. Comparison to the reported p16 cDNA sequence (Serrano, et al., Nature, supra) reveals that the reported sequence contains regions encoding for E. coli proteins and differs in its 5' region from the CDK4I gene by several base pairs, (see comparison contained in FIG. 3; the relevant portions of genomic CDK4I are shown along the bottom line while the Serrano, et al., partial sequence (5' region) is shown along the top line. Differences in the sequences are indicated by the absence of vertical connecting lines).

Genomic CDK4I was identified and characterized as described below. The CDK4I gene was believed to reside on chromosome 9p between the loci for MTAse and the interferon alpha ("INF-a") gene cluster. This location was suggested by the fact that many malignant cell lines with deletions in chromosome 9p either lack MTAse or have hemizygous or homozygous deletions of INF-a. In particular, a small 9p deletion identified in the T98G glioma cell line (ATCC Accession No. CRL 1690) centromeric to the INF-a loci was focused upon as a possible location for CDK4I.

As described in greater detail in Example I, the putative location for CDK4I was explored with a MTAse cDNA that was used to probe a human placenta lambda phage library (SEQ ID NO:14 contains the genomic nucleotide sequence for MTAse; see also, ATCC Accession Nos. 55536–55540). Starting with a 2 kilobase Hind III fragment (MTAse clone 7-2; ATCC Accession No. 55540), chromosome walking was performed and, through screening of subsequent lambda phage libraries, clones were isolated which encompassed the deleted region in T98G cells. The region of chromosome 9p21 between the loci for the MTAse gene and the INF-α gene was sequenced focusing on the deleted segment in T98G; the sequence is contained in FIG. 4(a) (SEQ ID NOS:17 and 18).

Figure 1:
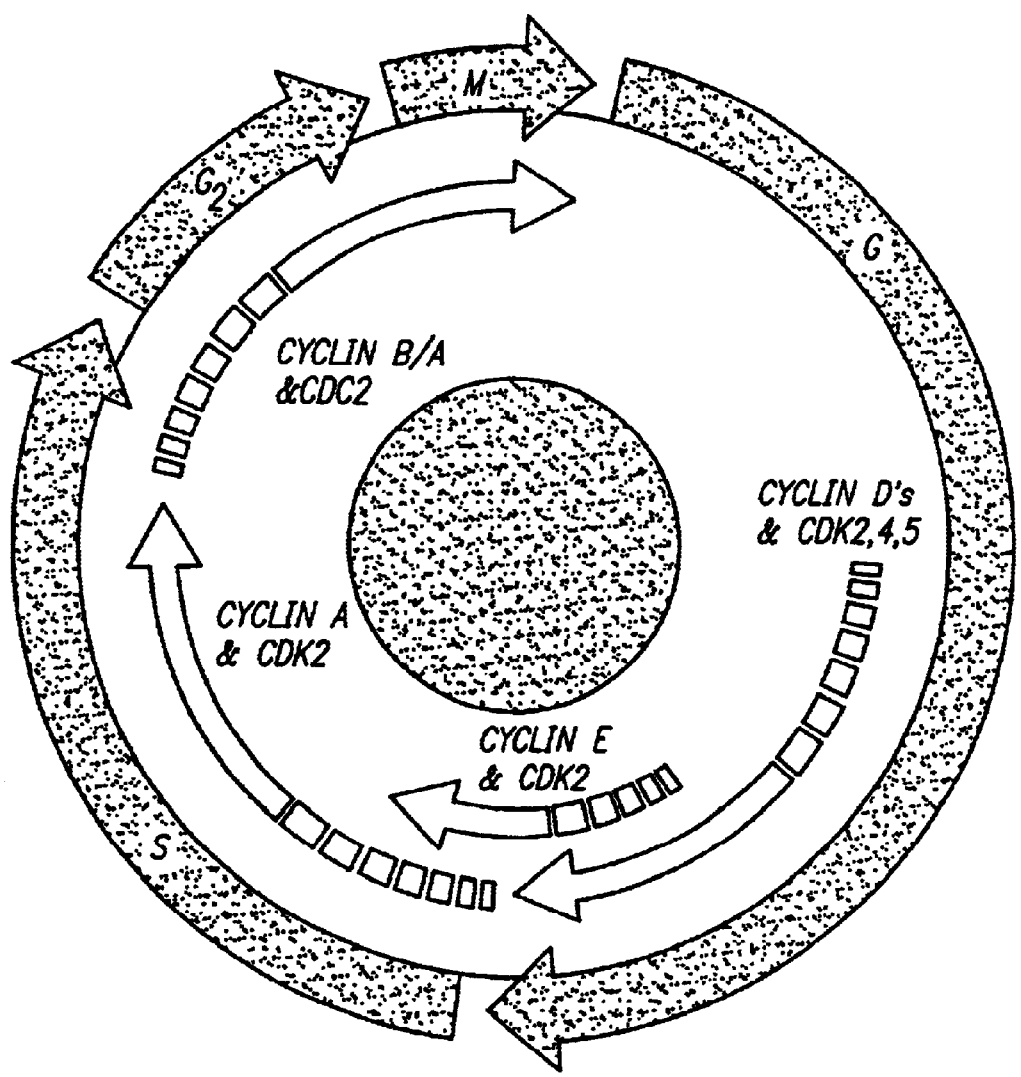
FIG. 1 depicts the phases from G1 through mitosis (M) of the growth cycle of a mammalian cell.
Figure 4B:
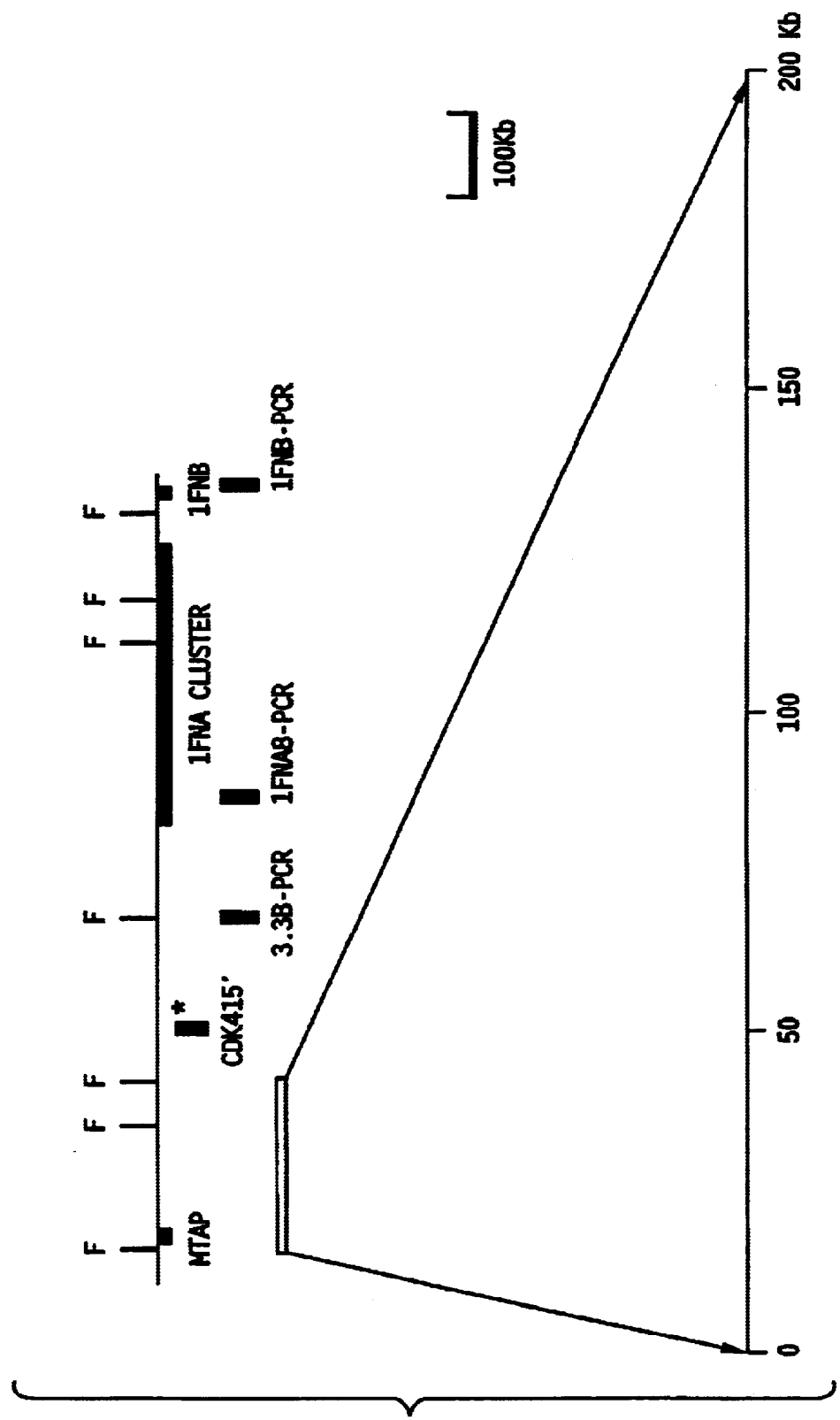
FIGS. 4 (a–b) depicts the region of chromosome 9p21 between the MTAse and INF-α gene loci, focusing on the deleted segment in T98G. FIG. (a) shows the nucleotide sequence of the deleted segment (SEQ ID NOS:17 and 18)

45 cancer cell lines were screened to determine the frequency of deletions of the putative tumor suppressor gene and other sites in region identified in FIG. 4(a). Data obtained from this assay are shown in FIG. 8. Introns from the two most frequently deleted sites are identified in FIG. 4(b) as sequence tagged site (STS) 54F and STS 5BS, which sites are separated by 50 kilobase region. Probes were designed to specifically bind to portions of the 50 kilobase region between STS 54F and STS 5BS (SEQ ID NOS:6 and 7). The most frequently deleted region was identified by a 19 kilobase lambda phage clone (10B1-10) (see, FIG. 4(a); SEQ ID NOS:17 and 18). As described in Example I, the CDK4I gene was found to reside in the region of chromosome 9 which corresponds to clone 10B1-10 (CDK4I3' and CDK4I') and a related clone 10A1 (CDK4I5').

The CDK4I gene is contained in two E. coli strains (containing, respectively, 10B1–10 and 10A1) on deposit with the American Type Culture Collection ("ATCC"), at P.O. Box 1549, Manassas, Va. 20108 deposited on Apr. 14, 1994 under Designation Nos. 69606 and 69607 (respectively, clone 10B1–10 [SEQ ID NO: 1] and 10A-10 [SEQ ID NO: 2]). However, no admission that this deposit was necessary to the enablement of this disclosure or any of the claims contained herein is made or intended.

As shown in FIG. 2 and SEQ ID NO's: 3–5, the CDK4I exon of the CDK4I gene has a 306 base pair open reading frame, the CDK4I3' exon has a short open reading frame corresponding to the last 15 base pairs of the coding region for CDK4I and the CDK4I5' exon has a 139 base pair open reading frame.

II. FREQUENCY OF DELETION OF THE CDK4I GENE IN CANCER CELL LINES

Many cancers cluster in families. For example, of approximately 30,000 new cases of cutaneous melanomas diagnosed annually in the United States, about 5–10% originate in a familial setting (see, Cannon-Albright, et al., Science, 258:1148–1152). The locus for familial melanoma has previously been identified as chromosome 9p21, a region that is reproducibly deleted in sporadic melanomas (Fountain, et aL, Proc.Natl.Acad.Sci.USA, 89:10557–10561, 1992). In addition, environmental factors, such as exposure to ultraviolet rays and cigarette smoking have been identified as major risk factors for the development of melanomas in the former case and of lung, bladder, head, neck, and larynx cancers. For example, abnormalities of chromosome 9p21 are very common in lung cancer cells (Nobori, et al., *Cancer Res.*, 53:1098–1101, 1993).

As described in Example II, to determine whether the CDK4I gene was present in, or deleted from, known cancer cell lines, probes corresponding to the CDK4I gene were used to rescreen the 45 cancer cell lines referred to above. The results of this assay are shown (in a hybridization blot) in FIG. 9. For reference, probes corresponding to the MTAse, INF-a and INF-b genes, as well as the 3.21, 2F, 54F, 71F, and 3.3B regions on chromosome 9 (see, FIG. 4 (*b*) and FIG. 5) were used to screen for the presence of those regions in the same cell lines. The complete results of this assay for all gene regions tested are tabulated by percentage deletion in Table 1 below, to wit; 61% of melanomas, 87% of gliomas, 36% of non-small lung cancers and 64% of leukemias were identified as having homozygous deletions of the CDK4I gene. These data indicate that human cells contain a single CDK4I gene that is deleted or rearranged in the majority of melanomas, gliomas, and leukemias, as well as more than a third of non-small cell lung cancers.

in a biological cell sample such as that heretofore subjected to histopathologic examination using techniques of light microscopy, such as the margins of a primary tumor or a regional lymph node. Thus, the target nucleotide sequence may be, for example, a mutant nucleotide, a restriction fragment length polymorphism (RFLP), a nucleotide deletion, a nucleotide substitution, or any other mammalian nucleic acid sequence of interest in such tissue specimens. As used herein the term "polymorphism" as applied to a target CDK4I nucleotide sequence shall be understood to encompass a mutation, a restriction fragment length polymorphism, a nucleic acid deletion, or a nucleic acid substitution.

For example, cells from a human patient who had been diagnosed as suffering from familial melanoma (specifically, dysplastic nevus syndrome) were identified as containing a nonsense mutation (i.e., a C to T transition) at position 166 of the CDK4I mRNA (see, FIG. 6 (SEQ ID NOS:19 and 20) and Example V). In addition, cells from a known leukemia cell line (U937; ATCC Accession No. 1593) were screened and found to contain an intragenic microdeletion of 18 base pairs in the CDK4I5' exon (see, FIG. 7 (SEQ ID NOS:21 and 22) and Example VI). Using the information contained in

TABLE 1

HOMOZYGOUS LOSS OF CHROMOSOME 9p LOCI IN HUMAN CANCER CELL LINES

| Cell Line (Number tested) | MTAP | 3.21 | 2F | 54F | CDK4I | 5BS | 71F | 3.3B | IFNA8 | IFNB |
|---|---|---|---|---|---|---|---|---|---|---|
| Melanoma (13) | 30.8 | 38.5 | 53.8 | 53.8 | 61.5 | 61.5 | 61.5 | 15.4 | 7.7 | 0 |
| Glioma (8) | 62.5 | 75.0 | 87.5 | 87.5 | 87.5 | 75.0 | 75.0 | 62.5 | 62.5 | 25.0 |
| Lung Cancer (11) | 27.3 | 27.3 | 27.3 | 27.3 | 45.5 | 45.5 | 45.5 | 9.1 | 9.1 | 0 |
| Leukemia (14) | 50.0 | 50.0 | 64.3 | 64.3 | 64.3 | 57.1 | 57.1 | 28.6 | 28.6 | 21.4 |

III. FREQUENCY AND IDENTITY OF POINT MUTATIONS OF THE CDK4I GENE IN TUMOR CELLS

As discussed in the background section above, the gene encoding the tumor suppressor p53 has been found to be deleted in certain cancers, thus allowing unchecked cellular proliferation to occur. Logically, if a gene encoding a tumor suppressor contains a polymorphism that compromises the activity of the suppressor, then tumors may develop over time even without deletion of the gene encoding the suppressor. In the particular case of the CDK4I gene, its presence on chromosome 9p21 suggests that both deletions and polymorphisms of the gene may contribute to the onset of certain familial and environmental cancers.

More specifically, the role of CDK4I in binding and inhibiting CDK4 indicates that an excessive level of kinases can be expected to develop within cells that harbor a CDK4I gene deletion or polymorphism that compromises the ability of CDK4I to inhibit CDK4. Thus, while deletions of the CDK4I gene will be indicative of a pre-malignancy or malignancy, polymorphisms in the gene (particularly polymorphisms in germline cells of persons with a familial history of 9p21-linked cancers) will be indicative of a cancer susceptibility to develop a "cancer condition" (i.e., a condition which is causatively related to excessive cellular levels of CDK4).

In its broadest sense, the present invention allows the detection of any polymorphism in, or deletion of, a CDK4I target nucleic acid sequence of diagnostic or therapeutic relevance, where the target nucleic acid sequence is present SEQ ID NOS:1 and 2 and techniques for identifying point mutations in genes which are well-known in the art and illustrated herein, those of ordinary skill in the art will be able to screen cell samples from particular 9p21-linked tumors for reproducible polymorphisms and/or deletions of CDK4I to determine genetic susceptibility to, as well as the existence of, a cancer condition as defined herein (particularly melanomas, gliomas, non-small cell lung cancers and leukemias).

In the case of deletions and polymorphisms, this information can be used to diagnose a pre-cancerous condition or existing cancer condition. Further, by quantitating the number of cells in successive cell samples which bear and acquire the deletion or polymorphism at separate locations in the body and/or over time, the progression of a cancer condition can be monitored. Similarly, where a deletion or polymorphism is found in a patient who has not yet developed symptoms of a cancer condition (particularly one who carries the abnormality in germline cells and/or has a family history of a particular cancer condition), the deletion or polymorphism will be indicative of a genetic susceptibility to develop the cancer condition. Such susceptibility can further be evaluated on a qualitative basis based on information concerning the prevalence, if any, of the cancer condition in the patients family history and the presence of other risk factors, such as exposure to environmental factors and whether the patient also carries cells having a deletion of the gene for MTAse.

To this end, preferred diagnostic techniques are described below, the use of which is illustrated in the Examples provided herein.

IV. METHODS FOR DETECTION OF DELETIONS AND POLYMORPHISMS IN THE CDK4I GENE

Amplification of the CDK4I gene is generally required to produce detectable amounts of any gene present in a biological cell sample; i.e., a fluid or tissue sample which includes a sample of germline cells (e.g., from blood, skin or hair follicles) or somatic cells in a malignant or pre-malignant lesion (e.g., from tissue biopsies, sputum or urinary specimens). Following amplification, point mutations may be detected by means known to those of ordinary skill in the art such as direct sequencing, or oligonucleotide hybridization under conditions that can detect a single base pair change. Also suitable are the techniques for gel electrophoresis of single strand conformation polymorphisms (known in the art as "SSCP"; see, e.g., Orita, et al., Proc.Natl.Acad,Sci.USA, 86:2766–2770,1989), heteroduplex analysis to detect mismatches between double stranded DNA (a suitable kit for this protocol is the "MDE Heteroduplex Kit" sold by AT Biochem of Malvern, Pa.), allele specific PCR (see e.g., Wu, et al, Proc.Natl.Acad.Sci.USA, 86:2757–2760, and restriction fragment length polymorphism analysis (known in the art as "RFLP"; see, e.g., Knowlton, et al., Nature, 318:380–382, 1985). Examples of the application of these techniques to detect polymorphisms in the CDK4I gene are provided infra; for further details, the disclosures of the references referred to in the preceding sentence are incorporated herein by this reference.

Detection of homozygous deletions of the CDK4I gene may be readily detected by known PCR techniques, as illustrated further below. However, it is possible for a person to be hemizygous for the CDK4I gene, in which case gene dosage analysis for each exon will be performed. Quantitative PCR techniques known in the art may be used to perform this analysis; a preferred technique is described below and in Kohsaka, et al, Nuc.Acids Res., 21:3469–3472, 1993. Examples illustrating the use of the preferred technique to detect point mutations in the CDK4I gene are provided infra; for further reference, the disclosures of the Kohsaka, et al., article and co-pending applications referred to in the preceding sentence are incorporated herein by reference.

The most preferred method for performance of qualtitative PCR to detect deletions and polymorphisms of the CDK4I gene involves use of the PCR-ELISA techniques described in infra and in Kohsaka, et al., supra. Although such PCR-ELISA methods are preferred for their sensitivity and simplicity, those of ordinary skill in the art will know of, or can readily ascertain, other suitable PCR assays (such as are described in "PCR Protocols", Innis, et al., eds., (Academic Press, 1990)).

A. General Methods for Use in PCR and PCR-based Assays

When is is desirable to amplify the CDK4I target nucleotide sequence before detection, such as a CDK4I nucleotide sequence containing a polymorphism, this can be accomplished using oligonucleotide(s) that are primers for amplification. These unique oligonucleotide primers are based upon identification of the lanking regions contiguous with the CDK4I nucleotide sequence containing the polymorphism.

In general, primers for use in PCR-based assays will embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Experimental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers for use in the PCR-based assays of the invention will be designed to be "substantially" complementary to each strand of mutant nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the mutant nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Kienow) or Taq DNA polymerase and nucleotides or ligases, results in newly synthesized + and − strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphosphoramidites are used gas starting materials and may be synthesized as described by Beaucage, et al.

(*Tetrahedron Letters*, 22:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

The nucleic acid from any biological cell sample, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified may be a fraction of a larger molecule or can be present initially as a discrete molecule, such that the specific sequence constitutes the entire nucleic acid. It is not necessary that the sequence to be amplified be present initially in a pure form; it may be a minor fraction of a complex mixture, such as contained in whole human DNA.

Where the target neoplastic nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP which is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (Ann. Rev. *Genetics*, 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C.

The agent for polymerization may be any compound or system which will function to accomplish the synthesis of primer extension products, including enzymes. Suitable enzymes for this purpose include, for example, *E. coli* DNA polymerase I, Taq polymerase, KIenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by Southern blot analysis, without using radioactive probes. In such a process, for example, a small sample of DNA containing a very low level of mutant nucleotide sequence is amplified, and analyzed via a Southern blotting technique. The use of non-radioactive probes or labels is facilitated by the high level of the amplified signal.

Nucleic acids having a mutation detected in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

B. Hybridization with Labelled Probes

In another diagnostic method of the invention, purified nucleic acid fragments containing intervening sequences or oligonucleotide sequences of 10–50 base pairs are radioactively labelled. The labelled preparations are used to probe nucleic acid from a biological cell sample by the Southern hybridization technique. Nucleotide fragments from a biological cell sample, before or after amplification, are separated into fragments of different molecular masses by gel electrophoresis and transferred to filters that bind nucleic acid. After exposure to the labelled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from the sample can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated mammalian nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an individual to be at low risk or high risk for a cancer condition, such as familial melanoma.

For the most part, the probe will be detectably labelled with an atom or inorganic radical, most commonly using radionuclides, but also heavy metals can be used. Conveniently, a radioactive label may be employed. Radioactive labels include $^{32}P$, $^{125}I$, $^3H$, $^{14}C$, $^{111}In$, $^{99m}Tc$, or the like. Any radioactive label may be employed which provides for an adequate signal and has sufficient half-life. Other labels include ligands, which can serve as a specific binding pair member for a labelled ligand, and the like. A wide variety of labels routinely employed in immunoassays can readily be employed in the present assay.

The choice of the label will be governed by the effect of the label on the rate of hybridization and binding of the probe to the target nucleotide sequence. It will be necessary that the label provide sufficient sensitivity to detect the amount of target nucleotide sequence available for hybridization. Other considerations will be ease of synthesis of the probe, availability of instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}P$-dNTP or terminal phosphate hydrolysis with alkaline phosphatase followed by labeling with radioactive $^{32}P$ employing $^{32}P$-NTP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionucleotide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2, 3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a biological cell sample is cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kD), polyvinylpyrrolidone, (about 250–500 kD) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, (*Proc. Nat. Acad. Sci.* 63:378, 1969); and John, et al., (*Nature*, 223:582, 1969). As improvements are made in hybridization techniques they can readily be applied in the method of the invention.

The amount of labelled probe present in the hybridization solution will vary widely, depending upon the nature of the label, the amount of the labelled probe that can reasonably bind to the filter, and the stringency of the hybridization. Generally, substantial excess over stoichiometric concentrations of the probe will be employed to enhance the rate of binding of the probe to the fixed target nucleic acid.

Various degrees of stringency of hybridization may be employed. The more severe the conditions, the greater the complementarily that is required for hybridization between the probe and the single stranded target nucleic acid sequence for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 80° C., usually 30° C. to 75° C. (see, generally, *Current Protocols in Molecular Biology*, Ausubel, ed., Wiley & Sons, 1989).

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific antifluorescent antibody. For example, horseradish peroxidase enzyme can be conjugated to this antibody to catalyze a chemiluminescent reaction. Production of light can then be seen on rapid exposure to film.

C. Preferred, Competitive PCR-based Assays

The preferred method for performance of quantitative PCR in the invention is a competitive PCR technique performed using a competitor template containing an induced mutation of one or more base pairs which results in the competitor differing in sequence (but not size) from the target CDK4I gene template. One of the primers is biotinylated or, preferably, aminated so that one strand (usually the antisense strand) of the resulting PCR product can be immobilized via an amino-carboxyl, amino-amino, biotin-streptavidin or other suitably tight bond to a solid phase support which has been tightly bound to an appropriate reactant. Most preferably, the bonds between the PCR product, solid phase support and reactant will be covalent ones, thus reliably rendering the bonds resistant to uncoupling under denaturing conditions.

Once the aminated or biotinylated strands of the PCR products are immobilized, the unbound complementary strands are separated in an alkaline denaturing wash and removed from the reaction environment. Sequence-specific oligonucleotides ("SSO's") corresponding to the target and competitor nucleic acids are labelled with a detection tag. The SSO's are then hybridized to the antisense strands in absence of competition from the removed unbound sense strands. Appropriate assay reagents are added and the degree of hybridization is measured by ELISA measurement means appropriate to the detection tag and solid phase support means used, preferably an ELISA microplate reader. The measured values are compared to derive target nucleic acid content, using a standard curve separately derived from PCR reactions amplifying templates including target and competitor templates.

This method is advantageous in that it is quantitative, does not depend upon the number of PCR cycles, and is not influenced by competition between the SSO probe and the complementary strand in the PCR product.

Alternatively, part of the polymerization step and all of the hybridization step can be performed on a solid phase support. In this method, it is an nucleotide polymerization primer (preferably an oligonucleotide) which is captured onto a solid phase support rather than a strand of the PCR products. Target and competitor nucleic acid PCR products are then added in solution to the solid phase support and a polymerization step is performed. The unbound sense strands of the polymerization product are removed under the denaturing conditions described above.

A target to competitor nucleic acid ratio can be determined by detection of labelled oligonucleotide SSO probes using appropriate measurement means (preferably ELISA readers) and standard curve as described supra. The efficiency of this method can be so great that a chain reaction in the polymerization step may be unnecessary, thus shortening the time needed to perform the method. The accuracy of the method is also enhanced because the final polymerization products do not have to be transferred from a reaction tube to a solid phase support for hybridization, thus limiting the potential for their loss or damage. If necessary for a particular sample, however, the PCR may be used to amplify the target and competitor nucleic acids in a separate reaction tube, followed by a final polymerization performed on the solid phase support.

An additional alternative to the above described techniques performs the polymerization step in a single step on a solid phase support. In this method, the PCR is performed to amplify the target (and where a quantitative analysis is desired, the competitor) nucleic acid on a solid phase support. Before the PCR is performed, primers (which correspond to the target and competitor nucleic acids) are tightly bound to the solid phase support. Two additional primers are placed into solution with the target nucleic acid (or three primers where a competitive template is present).

As the PCR begins, the templates do not interact with the bound primer to a substantial degree because template concentration is relatively low and the bound primer is not readily accessible. However, as the templates are amplified, more of the PCR products become bound to the solid phase via hybridization with the bound primer. In essence, therefore, the bound primers serve as hybridization probes for the PCR products formed by priming of the target and competitor nucleic acids. Once hybridization occurs, the hybridization primer elongates via the PCR.

Molecules capable of providing different, detectible signals indicative of the formation of bound PCR products known to those skilled in the art (such as the labels described supra as well as labelled nucleotide chromophores which will form different colors indicative of the formation of target and competitor PCR products) can be added to the reaction solution during the last few cycles of the reaction. The ratio between the target and competitor nucleic acids can also be determined by ELISA or other appropriate measurement means and reagents reactive with detection tags coupled to the 3' end of the immobilized hybridization primers. This method may also be adapted to detect whether a particular gene is present in the sample (without quantifying it) by performing a conventional noncompetitive PCR protocol.

Those of ordinary skill in the art will know, or may readily ascertain, how to select suitable primers for use in the above methods. For example, primers which will amplify the CDK4I gene and correspond to the CDK4I', CDK413' and CDK415' exons are described in SEQ.ID.Nos.8–13.

D. Single-strand Conformation Polymorphism Analysis

Techniques to detect DNA polymorphisms based on restriction fragment length polymorphism analysis (RFLP) and electrophoresis gel mobility shifts caused by single nucleotide substitution in single-stranded DNA (SSCP) have proved to be useful methods for distinguishing allelic variations at chromosomal loci. For example, RFLP has been used to detect genetic abnormalities present in cystic fibrosis and other hereditary disorders (see, e.g., Knowlton, et al., *Nature*, 318:380–382 [re use of RFLP to detect cystic fibrosis], and Shiraishi, et al., *Jpn.J.Cancer Res.*, 78:1302–1308, 1987 [re. performance of RFLP generally], the disclosures of which are incorporated herein by this reference to illustrate knowledge in the art concerning the use of RFLP). However, RFLP requires that the polymorphisms of interest be present in the recognition sequences for the corresponding restriction endonucleases or when deletion or insertion of a short sequence is present in the region detected by a particular probe. Therefore, SSCP is a preferred technique for detection of allele-specific polymorphisms.

The technique for performance of SSCP is well-known in the art (see, e.g., Orita, et at, *Genetics*, 86:2766–2770, 1989, the disclosure of which is incorporated herein by this reference to illustrate knowledge in the art concerning the use of SSCP). Generally, gene fragments or alleles of interest are denatured and subjected to electrophoresis in a neutral polyacrylamide gel. Single-stranded DNA's (or RNA copies thereof) are transferred to a membrane (by blotting) and hybridized with detectably labelled DNA probes for the fragments/alleles of interest. The relative speed in which the fragments/alleles of interest move in the gel ("mobility shift") is indicative of the presence or absence of base substitutions.

A particularly suitable SSCP technique is one-which uses the PCR is used to simultaneously amplify the target sequence and label it with a radioisotope or, preferably, a fluorescein molecule (using labelled primers in the PCR; i.e., "F-PCR-SSCP"). Most preferably, detection of bands of DNA in a polyacrylamide gel will be performed with an automatic DNA sequencer, which permits strict control of the gel at any desired temperature and allows for quantitative interpretation of the resulting data (based on the proportionality of the heights of the peaks in the fluorogram to the intensity of the fluorescence emitted by the labelled DNA). For a summary of the known method for performance of F-PCR-SSCP, those of skill in the art may wish to consult Makino, et at, *PCR Methods and Appins.*, 2:10–13 (Cold Spring Harbor Lab., 1992), the disclosure of which is incorporated herein by this reference to illustrate knowledge in the art concerning F-PCR-SSCP.

cl E. Allele-specific Enzymatic Amplification of Genomic DNA

A simple, and therefore preferred, method of detecting polymorphisms in genomic DNA is a technique which is based on a allele-specific PCR (ASPCR). In ASPCR, two allele-specific oligonucleotide primers (such as those described in SEQ ID NO's: 8–13), one of which is specific for the suspected and/or known mutated allele, the other of which is specific for the "normal" allele, are used in the PCR with genomic DNA templates and another primer which is complementary to both alleles. Under the proper annealing temperature and PCR conditions, the primers will only direct amplification of their complementary allele, thus allowing for the determination of genotypes in nucleic acid samples obtained from human tissue. More particularly, suitable temperatures for this PCR are about 55° C. for the annealing cycles, about 72° C. for the polymerization cycles, and about 94° C. for the heat-denaturation cycles.

For further details concerning performance of the ASPCR, those of skill in the art may wish to consult Wu, et al., *Proc.Natl.Acad.Sci. USA*, 86:2757–2760, 1989, the disclosure of which is incorporated herein by this reference.

F. Indirect Detection of Gene Deletions Based on the Absence of CDK4I In a Biological Cell Sample In a normal, non-malignant cell, CDK4I can be expected to be present, usually in bound form; i.e., in a complex of CDK4I, CDK4, cyclin D and other molecules, such as a cell nuclear antigen. Methods for indirect detection of a deletion of the gene for CDK4I based on the absence of the CDK4 protein (as determined by, preferably, immunoassay) are described in further detail below at Section VIII.

V. ISOLATION AND PURIFICATION OF CDK4I

The term "substantially pure" as used herein denotes a protein which is substantially free of other compounds with which it may normally be associated in vivo. In the context of the invention, the term refers to homogenous CDK4I, which homogenicity is determined by reference to purity standards known to those of ordinary skill in the art (e.g., purity sufficient to allow the N-terminal amino acid sequence of the protein to be obtained).

Substantially pure CDK4I may be obtained from tissue homogenates (containing "normal" cells; i.e., those cells which contain the CDK4I gene), through microbial expression, by synthesis, or by purification means known to those skilled in the art, such as affinity chromatography. Such techniques may be utilized to obtain biologically active peptide fragments of CDK4I. In this context, "biologically active peptide fragments" refers to fragments which contain a binding domain for CDK4.

Determination that a CDK4I fragment contains a CDK4 binding domain may be made by use of any of several methods known to those skilled in the art, including determination of the binding kinetics and affinity of the fragment for CDK4 as well as inhibition studies using anti-CDK4 antibodies (see, e.g., Xiong, et al., *Genes Dev.*, 7:1572–1583, 1993, the disclosure of which is incorporated herein by this reference to illustrate a standard method for production of anti-CDK4 antibodies; other suitable methods for antibody production which may be adapted to produce anti-CDK4 antibodies are described infra). Minor modifications of the primary amino acid sequence of CDK4I (which may be readily derived from SEQ.ID.Nos. 1–2) may result in variants which have substantially equivalent activity as compared to the specific CDK4I protein described herein. Such modifications may be deliberate, as by site-directed mutagenesis, or may be spontaneous. All of the variants produced by these modifications are included herein as long as biological activity present in the original protein still exists. For purposes of this disclosure, such variants shall. be generally considered to be "functional variants". Functional amino acid sequence variants of CDK4I may fall into one or more of three classes; substitutional, insertional or deletional variants. Such variants ordinarily are prepared by site-specific mutagenesis of nucleotides in the DNA encoding CDK4I hereby producing DNA encoding the variant, and thereafter expressing the DNA in recombinant cell culture. However, variant CDK4I and CDK4I fragments having up to about 100–150 residues may be conveniently prepared by in vitro synthesis.

Amino acid sequence variants are ordinarily characterized by the intended nature of the variation, but such variants also include naturally occurring allelic or interspecies variation of the CDK4I amino acid sequence. The variants typically exhibit the same qualitative biological activity as the naturally-occurring analogue, although variants may also be selected in order to modify the characteristics of CDK4I as will be more fully described below.

While the site for introducing an amino acid sequence variation is predetermined, the mutation per se need not be predetermined. For example, in order to optimize the performance of a mutation at a given site, random mutagenesis may be directed at the target codon or region and the expressed CDK4I variants screened for the optimal combination of desired activity. Techniques for making substitution mutations at particular sites in DNA having a known sequence are well known, for example M13 primer mutagenesis. Amino acid substitutions are typically of single residues; insertions usually will be on the order of about from 1 to 10 amino acid residues; and deletions will usually range about from 1 to 30 residues. Deletions or insertions preferably are made in adjacent pairs, i.e., a deletion of 2 residues or insertion of 2 residues.

Substitutions, deletions, insertions or any combination thereof may be combined to arrive at a final construct. Obviously, the mutations that will be made in the DNA encoding the variant CDK4I must not place the sequence out of reading frame (see, SEQ.ID.Nos: 1–2).

Substitutional variants are those in which at least one residue in SEQ ID No. 2 has been removed and a different residue inserted in its place. These may be made to eliminate glycosylation sites in the sequence, to alter the pH, to increase the stability of the protein, or to accomplish other desirable modifications in the protein, which modifications will be apparent to those of ordinary skill in the art. For example, oxidative stability of CDK4I may be achieved by deletion of cysteine or other labile residues. Deletion or substitution of potential proteolysis sites can also be accomplished by deleting such residues or substituting a glutaminyl or histidyl residue.

Insertional amino acid sequence variants of CDK4I are those in which one or more amino acid residues are introduce into a predetermined site in the target receptor. Most commonly, insertional variants are fusions of heterologous proteins or polypeptides to the amino or carboxyl terminus of the protein to be varied. For example, immunogenic CDK4I derivatives may be made by fusing an immunogenic polypeptide to the target sequence by cross-linking in vitro or by recombinant cell culture transformed with DNA encoding the fusion. Such immunogenic polypeptides preferably are bacterial polypeptides such as trpLE, beta-galactosidase and the like, together with their immunogenic fragments. CDK4I of the invention also includes amino acid sequence mutants, glycosylation variants and covalent or aggregative conjugates with other chemical moieties. Covalent derivatives of CDK4I may also be prepared by linkage of functional moieties to groups which are found in the receptor's amino acid side chains or at the N, or C-termini, by means known in the art. These derivatives may, for example, include aliphatic esters or amides of the carboxyl terminus or residues containing carboxyl side chains, O-acyl derivatives of hydroxyl group-containing residues, and N-acyl derivatives of the amino terminal amino acid or amino-group containing residues, e.g. lysine or arginine.

Another group of derivatives are covalent conjugates of CDK4I and CDK4I fragments with other proteins or polypeptides. These derivatives may be synthesized by one of ordinary skill in the art in recombinant culture as N, or C-terminal fusions or by the use of dysfunctional agents known per se for use in cross-linking proteins to insoluble matrices through reactive side-groups.

Covalent or aggregative derivatives will be useful as immunogens, reagents in immunoassay or for affinity purification of CDK4I. For example, CDK4I insolubilized by covalent bonding to cyanogen -bromide-activated "SEPHA-ROSE" (agarose tradename) by known methods or adsorbed to polyoefin surfaces may be used in an assay or in purification of anti-CDK4I antibodies or CDK4I ligand.

With reference to SEQ.ID.Nos: 1–2, CDK4I protein and peptides can be identified and synthesized by such commonly used methods as t-BOC or FMOC protection of alpha-amino groups. Both methods involve stepwise syntheses whereby a single amino acid is added at each step starting from the C terminus of the peptide (see, Coligan, et al., *Current Protocols in Immunology*, Wiley Interscience, 1991, Unit 9). Peptides of the invention can also be synthesized by various well known solid phase peptide synthesis methods, such as those described by Merrifield (*J. Am. Chem. Soc.*, 85:2149, 1962), and Stewart and Young (*Solid*

*Phase Peptides Synthesis*, Freeman, San Francisco, 1969, pp 27–62), using a copoly (styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on a "SEPHADEX G-15" or "SEPHAROSE" affinity column. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Compositions comprising CDK4I may include such substances as the stabilizers and excipients described below, predetermined amounts of proteins from the cell or organism that served as the source of the CDK4I gene, proteins from other than CDK4I source cells or organisms, and synthetic polypeptides such as poly-L-lysine. Recombinant CDK4I which is expressed in allogeneic hosts will of course be expressed completely free of gene source proteins. For example, expression of human CDK4I in Chinese Hamster Ovary (CHO) cells or other nonhuman higher mammalian cells results in a composition where the receptor is free of contaminating agents and human proteins.

VI. CDK4I DNA SEQUENCES AND EXPRESSION PRODUCTS

The invention also provides polynucleotides which encode CDK4I. As used herein, "polynucleotide" refers to a polymer of deoxyribonucleotides or ribonucleotides, both single-stranded (including sense and antisense strands) and double-stranded, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include genomic DNA, RNA and cDNA sequences. A polynucleotide sequence can be deduced from the genetic code, however, the degeneracy of the code must be taken into account. Polynucleotides of the invention include sequences which are degenerate as a result of the genetic code.

As described in further detail below, polynucleotide sequences encoding CDK4I can be expressed in either prokaryotes or eukaryotes. Hosts can include microbial yeast, insect and mammalian organisms. Methods of expressing DNA sequences having eukaryotic or viral sequences in prokaryotes are well known in the art. Biologically functional viraliand plasmid DNA vectors capable of expression and replication in a host are known in the art. Such vectors (i.e., "recombinant expression vectors") are used to incorporate DNA sequences of the invention. These sequences may also be contained in "host cells", i.e., transformed cells such as CHO and COS cells (e.g., ATCC Accession No. CRL 1651) for use in gene expression.

DNA encoding CDK4I is obtained from sources other than humans by a) obtaining a cDNA library from mammalian tissue b) conducting hybridization analysis with labelled DNA encoding human growth hormone receptor and binding protein or fragments thereof (usually, greater than 100 bp) in order to detect clones in the CDNA library containing homologous sequences, and c) analyzing the clones by restriction enzyme analysis and nucleic acid sequencing to identify full-length clones. If full length clones are not present in the library, then appropriate fragments may be recovered from the various clones and ligated at restriction sites common to the clones to assemble a full-length clone.

DNA which encodes CDK4I is obtained by chemical synthesis, by screening reverse transcripts of mRNA from placental cells or cell line cultures, or by screening genomic libraries from any cell. Also included within the scope of the invention is nucleic acid which may not encode CDK4I but which nonetheless is capable of hybridizing with DNA encoding CDK4I under low stringency conditions (e.g. "primers" or "probes"). The probes and primers of the invention will generally be oligonucleotides; i.e., either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated. Such oligonucleotides may be detectably labelled with a detectable substance such as a fluorescent group, a radioactive atom or a chemiluminescent group by known methods and used in conventional hybridization assays. Such assays are employed in in vitro diagnosis, such as detection of CDK4I DNA or mRNA in tissue samples.

In general, prokaryotes are used for cloning of DNA sequences in constructing CDK4I expressing recombinant expression vectors. For example, *E. coli* K12 strain 294 (ATCC Accession No. 31446) may be particularly useful. Prokaryotes also are used for expression. The aforementioned strain, as well as *E. coli* W3110 (ATTC Accession No. 27325), bacilli such as *Bacillus subtilus*, and other enterobacteriaceae such as *Salmonella typhimurium* or *Serratia marcescans*, and various pseudomonas species may also be used for expression.

In general, plasmid vectors which may be used in the invention contain promoters and control sequences which are derived from species compatible with the host cell. The vector ordinarily carries a replication site as well as marker sequences which are capable of providing phenotypic selection in transformed cells. For example, *E. coli* is typically transformed using pBR322, a plasmid derived from an *E coli* species (Bolivar, et al., *Gene*, 2:95, 1977). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang, et al., *Nature*, 275:615, 1978; and Goeddel, et al., *Nature*, 281:544, 1979), alkaline phosphatase, the tryptophan (trp) promoter system (Goeddel, *Nucleic Acids Res.*, 8:4057,1980) and hybrid promoters such as the taq promoter (de Boer, et al., *Proc. Natl. Acad. Sci. USA*, 80:21–25, 1983). However, other functional bacterial promoters are suitable. Their nucleotide sequences are generally known in the art, thereby enabling a skilled worker to ligate them to DNA encoding CDK4I (Siebenlist et al., *Cell*, 20:269, 1980) using linkers or adapters to supply any required restriction sites.

In addition to prokaryotes, eukaryotic microbes such as yeast cultures may also be used. *Saccharomyces cerevisiae*, or common baker's yeast is the most commonly used eukaryotic microorganism, although a number of other strains are commonly available.

Suitable promoting sequences for use with yeast hosts include the promoters for 3-phosphoglycerate kinase (Hitzeman, et al., *J. Biol. Chem.*, 255:2073, 1980) or other glycolytic enzymes (Hess, et al. *J. Adv. Enzyme Reg.* 7:149, 1968; and Holland, *Biochemistry*, 17:4900, 1978) such as enolase, glyceralde-hyde-3-phosphate dehydrogenase, hexokinase, pyruvate decarboxylase, phosphofructokinase, glucose-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degraded enzymes associated with nitrogen metabolism, metallothionine, glyceraldehyde-3-phosphate dehydrogenase, and enzymes responsible for maltose and galactose utilization. Yeast enhancers also are advantageously used with yeast promoters.

"Control region" refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription of many genes is a CCAAT region where X may be any nucleotide. At the 3' end of most eukaryotic genes is an AATAAA sequence which may be the signal for additional of the poly A tail to the 3' end of the transcribed mRNA.

Preferred promoters controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters, e.g. beta actin promoter. The early and later promoters of the SV40 virus are conveniently obtained as an SV40 restriction fragment which also contains the SV40 viral origin of replication (Fiers, et al., *Nature*, 273:113, 1978). The immediate early promoter of the human cytomegalovirus is conveniently obtained as a Hindlil E restriction fragment (Greenaway, et al., *Gene*, 18:355–360, 1982). Promoters from the host cell or related species also are useful herein.

Transcription of a DNA encoding CDK4I by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins, et al., *Proc.NatL.Sci.Acad.USA*, 78:993, 1981) and 3' (Lusky, et al., *Mol. .Cell Bio.*, 3:1108, 1983) to the transcription unit, and within an intron (Banerji, et al., *Cell*, 33:729, 1983) as well as within the coding sequence itself (Osborne, et al., *Mol.Cell Bio.*, 4:1293 1984). Many enhancer sequences are now known from mammalian gene (globin, elastase, albumin, α-feto-protein and insulin). Typically, however, an enhancer from a eukaryotic cell virus will be used. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. Expression vectors may also contain a selection gene, also termed a selectable marker. Examples of suitable selectable markers for mammalian cells which are known in the art include dihydrofolate reductase (DHFR), thymidine kinase or neomycin. When such selectable markers are successfully transferred into a mammalian host cell, the transformed mammalian host cell can survive if placed under selective pressure, (i.e., by being conferred with drug resistance or genes altering the nutrient requirements of the host cell).

Suitable host cells for transformation with and expression of the vectors of this invention encoding CDK4I in higher eukaryotes include: monkey kidney CV1 line transformed by SV40 (ATCC CRL 1651); human embryonic kidney line (Graham, F. L., et al., *J. Gen Virol.*, 36:59, 1977); baby hamster kidney cells (ATCC CCL 10); chinese hamster ovary-cells-DHFR (Urlaub and Chasin, *Proc. Nat'l Sci. Acad. USA*, 77:4216, 1980); mouse sertoli cells (Mather, J. P., *Biol.Reprod.*, 23:243–251, 1980); monkey kidney cells (ATCC CCL 70); african green monkey kidney cells (ATCC CRL-1587); human cervical carcinoma cells (ATCC CCL 2); canine kidney cells (ATCC CCL 34); buffalo rat liver cells (ATCC CRL 1442); human lung cells (ATCC CCL 75); human liver cells (HB 8065); mouse mammary tumor (ATCC CCL51); and TRI cells (Mather, et al., *Annals N.Y. Acad. Sci.*, 383:44–68, 1982).

"Transformation" means introducing DNA into an organism so that the DNA is replicable, either as an extrachromosomal element or by chromosomal integration, such as described in Graham, et al., *Virology*, 52:456–457, 1973. However, other methods for introducing DNA into cells such as by nuclear injection or by protoplast fusion may also be used. If prokaryotic cells or cells which contain substantial cell wall constructions are used, transfection may be achieved by means well known in the art such as calcium treatment using calcium chloride as described by Cohen, F. N., et al., (*Proc.Nat'l Acad.Sci. USA*, 69:2110, 1972). A particularly convenient method of transforming host cells is by lipofection using, for example, the liposomal product or DOTMA (a trademarked product of Bethesda Research Labs, Gaithersberg, Md.).

"Transfection" refers to the taking up of an expression vector by a host cell whether or not any coding sequences are in fact expressed. Numerous methods of transfection are known to the ordinarily skilled artisan using, for example, CaPO$_4$ or electroporation. Successful transfection is generally recognized when any indication of the operation of the transfected vector occurs within the host cell.

Construction of suitable vectors containing the desired coding and control sequences employ standard ligation techniques. Isolated plasmids or DNA fragments are cleaved, tailored, and relegated in the form desired to form the plasmids required.

For example, for analysis to confirm correct sequences in plasmids constructed, the ligation mixtures may be used to transform a host cell and successful transformants selected by ampicillin or tetracycline resistance where appropriate. Plasmids from the transformants are prepared, analyzed by restriction and/or sequenced by, for example, the method of Messing, et al., (*Nucleic Acids Res.*, 9:309, 1981), the method of Maxam, et al., (*Methods in-Enzymology*, 65.499, 1980), or other suitable methods which will be known to those skilled in the art. Size separation of cleaved fragments is performed using conventional gel electrophoresis as described, for example, by Maniatis, et al., (*Molecular Cloning*, pp. 133–134, 1982).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

With reference to SEQ ID NO's: 1–2, production of polynucleotides by the aforementioned techniques is well within the skill of one of ordinary skill in the art. The invention therefore encompasses CDK4I polynucleotides obtained by such techniques.

VII. CDK4I ANTIBODIES

The invention also encompasses polyclonal and monoclonal antibodies which specifically bind to CDK4I. Such antibodies can be biologically produced through immunization of a mammal with CDK4I (including antigenic fragments thereof and fusion proteins), hereafter "immunogenic CDK4I".

A multiple injection immunization protocol is preferred for use in immunizing animals with immunogenic CDK4I (see, e.g., Langone, etal., eds., "Production of Antisera with Small Doses of Immunogen: Multiple Intradermal Injections", *Methods of Enzymology*, Acad. Press, 1981). For example, a good antibody. response can be obtained in rabbits by intradermal injection of 1 mg of immunogenic CDK4I emulsified in Complete Freund's Adjuvant followed several weeks later by one or more boosts of the same antigen in incomplete Freund's Adjuvant.

If desired, immunogenic CDK4I molecules may be coupled to a carrier protein by conjugation using techniques which are well-known in the art. Such commonly used carriers which are chemically coupled to the molecules include keyhole limpet hemocyanin (KLH), thyroglobulin, bovine serum albumin (BSA), and tetanus toxoid. The coupled molecule is then used to immunize the animal (e.g., a mouse or a rabbit).

Polyclonal antibodies produced by the immunized animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (see, for example, Coligan, et al., *Current Protocols in Immunology*, Unit 9, (Wiley lnterscience, 1991)).

For their specificity and ease of production monoclonal antibodies will be preferred for use in detecting CDK4I in analyte samples (e.g., tissue samples and cell lines). For preparation of monoclonal antibodies, immunization of a mouse or rat is preferred. The term "antibody" as used in this invention is meant also to include intact molecules as well as fragments thereof, such as for example, Fab and F(ab$^1$)$_2$, which are capable of binding the epitopic determinant. Also, in this context, the term "mAb's of the invention" refers to monoclonal antibodies with specificity for CDK4I.

The general method used for production of hybridomas secreting monoclonal antibodies ("mAb's") is well known (Kohler and Milstein, *Nature*, 256:495, 1975). Briefly, as described by Kohler and Milstein, the technique comprised isolation of lymphocytes from regional draining lymph nodes of five separate cancer patients with either melanoma, teratocarcinoma or cancer of the cervix, glioma or lung. The lymphocytes were obtained from surgical specimens, pooled, and then fused with SHFP-1. Hybridomas were screened for production of antibody which bound to cancer cell lines. An equivalent technique can be used to produce and identify mAb's with specificity for CDK4I.

Confirmation of CDK4I specificity among mAbs of the invention can be accomplished using relatively routine screening techniques (such as the enzyme-linked immunosorbent assay, or "ELISA") to determine the elementary reaction pattern of the mAb of interest.

It is also possible to evaluate an mAb to determine whether is has the same specificity as mAb of the invention without undue experimentation by determining whether the mAb being tested prevents a mAb of the invention from binding to CDK4I. If the mAb being tested competes with the mAb of the invention, as shown by a decrease in binding by the mAb of the invention, then it is likely that the two monoclonal antibodies bind to the same or a closely related epitope.

Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention. As noted further below, this same general technique may also be used to screen potential CDK4I ligand.

Methods known in the art also allow antibodies which will specifically bind a preselected ligand to be identified and isolated from antibody expression libraries. For example, a method for the identification and isolation of an antibody binding domain which exhibits binding with a peptide of the invention is the bacteriophage y vector system. This vector system has been used to express a combinatorial library of Fab fragments from the mouse antibody repertoire in Escherichia coli (Huse, et al., *Science*, 246:1275–1281, 1989) and from the human antibody repertoire Mullinax, et al., (*Proc.Nat'lAcad.Sci. USA*, 87:8095–8099, 1990). As described therein, antibodies which bound a preselected ligand were identified and isolated from these antibody expression libraries. This methodology can also be applied to hybridoma cell lines expressing monoclonal antibodies which bind for a preselected ligand.

This invention further provides chimeric antibodies of the CDK4I-specific antibodies described above or biologically active fragments thereof. As used herein, the term "chimeric antibody" refers to an antibody in which the variable regions of antibodies derived from one species are combined with the constant regions of antibodies derived from a different species or alternatively refers to CDR grafted antibodies. Chimeric antibodies are constructed by recombinant DNA technology and are described, for example, in Shaw, et al., *J. Immun.*, 138:4534, 1987, and Sun, LK., et al., *Proc.Nat-l.Acad.Sci. USA*, 84:214–218, 1987.

In addition, methods of producing chimeric antibody molecules with various combinations of "humanized" antibodies are known in the art and include combining murine variable regions with human constant regions (Cabily, et al., *Proc.Natl.Acad.Sci USA*, 81:3273, 1984), or by grafting the murine-antibody complementary determining regions (CDRs) onto the human framework (Riechmann, et al., *Nature*, 322:323, 1988).

Any of the above described antibodies or biologically active antibody fragments can be used to generate CDR grafted and chimeric antibodies. "CDR" or "complementarty determining region" or "hypervariable region" are each defined as the amino acid sequences on the light and heavy chains of an antibody which form the three-dimensional loop structure that contributes to the formation of the antigen binding site.

As used herein, the term "CDR grafted" antibody refers to an antibody having an amino acid sequence in which at least parts of one or more CDR sequences in the light and/or variable domain have been replaced by analogous parts of CDR sequences from an antibody having a different binding specificity for a given antigen or receptor.

The terms "light chain variable region" and "heavy chain variable region" refer to the regions or domains at the N-terminal portion of the light and heavy chains respectively which have a varied primary amino acid sequence for each antibody. The variable region of the antibody consists of the amino terminal domain of the light and heavy chains as they fold together to form a three-dimensional binding site for an antibody.

The analogous CDR sequences are said to be "grafted" onto the substrate or recipient antibody. The "donor" antibody is the antibody providing the CDR sequence, and the antibody receiving the substituted sequences is the "substrate" antibody. One of skill in the art can readily produce these CDR grafted antibodies using the teachings provided herein in combination with methods well known in the art (see Borrebaeck, *Antibody Engineerng: A Practical Guide* (W. H. Freeman and Company, New York, 1992)).

Under certain circumstances, monoclonal antibodies of one isotype might be more preferable than those of another in terms of their diagnostic or therapeutic efficacy. For example, from studies on antibody-mediated cytolysis it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of the target cells. Particular isotypes of a monoclonal antibody of different isotype, by using the sib selection technique to isolate class-switch variants (Steplewski, et al., *Proc. Nat'l Acad. Sci. USA*, 82:8653, 1985; Spira, et al., *J. Immunol. Methods*, 74:307, 1984).

The invention also encompasses cell lines which produce monoclonal antibodies of the invention. The isolation of cell lines producing monoclonal antibodies of the invention can be accomplished using routine screening techniques which permit determination of the elementary reaction pattern of the monoclonal antibody of interest. Thus, if a monoclonal antibody being tested binds and neutralizes the activity associated with the specific peptide, for example binds CDK4I and blocks CDK4I-mediated biological activity, then the monoclonal antibody being tested and the monoclonal antibody produced by the cell lines of the invention are equivalent.

By using the monoclonal antibodies of the invention, it is possible to produce anti-idiotypic antibodies which can be used to screen monoclonal antibodies to identify whether the antibody has the same binding specificity as a monoclonal antibody of the invention. These antibodies can also be used for immunization purposes (Herlyn, et al., *Science*, 232:100, 1986). Such antiidiotypic antibodies can be produced using well-known hybridoma techniques (Kohler and Milstein, *Nature*, 256:495, 1975).

An anti-idiotypic antibody is an antibody which recognizes unique determinants present on the monoclonal antibody produced by the cell line of interest. These determinants are located in the hypervariable region of the antibody. It is this region (paratope) which binds to a given epitope and, thus, is responsible for the specificity of the antbody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for a monoclonal antibody of the invention produced by a cell line which was used to immunize the second animal, it is now possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

VIII. IMMUNOLOGICAL USE OF Anti-CDK4I ANTIBODIES

Once produced as described supra, anti-CDK4I antibodies may be used diagnostically (e.g., to detect CDK4I in a biological cell sample or monitor the level of its expression). Preferably, to detect the CDK4I protein in premalignant somatic cells, a suitable cell sample will be derived from skin biopsies, sputum specimens, or urinary specimens. Germline cells may be obtained from any convenient source, such as skin, blood, or hair follicles.

CDK4I may be detected and/or bound using anti-CDK4I antibodies in either liquid or solid phase immunoassay formats (when bound to a carrier). Examples of well-known carriers for use in solid-phase assay formats include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. Examples of types of immunoassays which can utilize monoclonal antibodies of the invention are competitive and non-competitive immunoassays in either a direct or indirect format.

Specific examples of such immunoassays are the radioimmunoassay (RIA) and the sandwich (immunometric) assay. Binding CDK4I using the anti-CDK4I antibodies of the invention can be done utilizing immunoassays which are run in either the forward, reverse, or simultaneous modes, including immunohistochemical assays on physiological samples. Those of skill in the art will know, or can readily discern other immunoassay formats without undue experimentation.

The anti-CDK4I antibodies of the invention may also be detectably labelled. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the anti-CDK4I antibodies of the invention, or will be able to ascertain such, using routine experimentation. Furthermore, the binding of these labels to the anti-CDK4I antibodies of the invention can be done using standard techniques common to those of ordinary skill in the art. Another labeling technique which may result in greater sensitivity consists of coupling the antibodies to low molecular weight haptens. These haptens can then be specifically detected by means of a second reaction. For example, it is common to use haptens for this purpose such as biotin, which reacts with avidin.

The anti-CDK4I antibodies of the invention can also be used for in vivo diagnosis, such as to identify a site of infection or inflammation or to monitor a particular therapy. In using the anti-CDK4I antibodies of the invention for the in vivo detection of antigen having a peptide of the invention, the detectably labeled monoclonal antibody is given in a dose which is diagnostically effective. The term "diagnostically effective" means that the amount of detectably labeled anti-CDK4I antibody is administered in sufficient quantity to enable detection of the site having cells which express CDK4I.

The concentration of detectably labeled anti-CDK4I antibody which is administered should be sufficient such that the binding to a peptide of the invention is detectable compared to the background. Further, it is desirable that the detectably labeled antibody be rapidly cleared from the circulatory system in order to give the best target-to-background signal ratio.

As a rule, the dosage of detectably labeled anti-CDK4I antibody for in vivo diagnosis will vary depending on such factors as age, sex, and extent of disease of the individual. The dosage of antibody can vary from about 0.01 mg/m$^2$, to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tissue, and other factors known to those of skill in the art.

For in vivo diagnostic imaging, the type of detection instrument available is a major factor in selecting a given radioisotope. The radioisotope chosen must have a type of decay which is detectable for a give type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

The anti-CDK4I antibodies of the invention can be used in vitro and in vivo to monitor the course of disease therapy. For example, the CDK4I protein and peptide fragments of the invention may be used diagnostically in biological fluids and tissues to monitor the fate of anti-CDK4I antibodies used therapeutically as described below.

IX. THERAPEUTIC USES OF CDK4I

A. Administration of Pharmaceutical Compositions

Because cancers related to deletion of, or polymorphisms in, the gene for CDK4I are causatively related to the loss of, or reduction in, the inhibitory activity of CDK4I, administration of a therapeutically effective amount of CDK4I will delay, if not also prevent, the progression or onset of such cancers. Also, because many CDK4I gene deletions and polymorphisms are present in cells which are also genetically deficient in the ability to produce MTAse, then combined therapeutic regimes directed to providing the patient with therapeutically effective amounts of both CDK4I and MTAse will also be of benefit in delaying, if not also preventing, the progression or onset of such cancers.

These ends may be achieved through the direct administration of purified, synthetic or recombinant CDK4I and, where appropriate, MTAse. Alternatively, these ends may be achieved by gene therapy, particularly gene replacement therapy. Means for the production of purified, synthetic or recombinant CDK4I and/or MTAse will be known to, or can be readily ascertained, by one of ordinary skill in the art in combination with the information concerning CDK4I and MTAse provided in this disclosure (i.e., at SEQ.ID.Nos 1–5 and 14; see also, FIGS. 2 (a–b) (showing the genomic nucleotide sequence for the CDK4I gene, with exons underlined; and, FIG. 10, showing the genomic nucleotide sequence for the MTAse gene, with the exons underlined).

CDK4I compositions are prepared for administration by mixing CDK4I having the desired degree of purity with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients. Such compositions may also be lyophilized and will be pharmaceutically acceptable; i.e., suitably prepared and approved for use in the desired application.

Given that CDK4I will be absent or of reduced efficacy in malignant or premalignant cells, cells having that condition will be the preferred targets for introduction of the CDK4I compositions of the invention. Where, however, the CDK4I abnormalities to be treated are In germline or somatic cells with no other detectable signs of malignancy, administration may be by any enteral or parenteral route in dosages which will be varied by the skilled clinician depending on the patient's presenting condition and the therapeutic ends to be achieved.

In this regard, "biological activity" of CDK4 refers to the enzymatic reaction stemming from the binding of CDK4 to cyclin D and related molecules during the growth cycle of a human cell. Further, "biological activity" of CDK4I refers to the inhibition of the biological activity of CDK4 stemming from the binding of CDK4 by CDK4I.

Generally, therefore, a "therapeutically effective dosage" of a CDK4I composition will be a dosage sufficient to inhibit the biological activity of CDK4 in human cells wherein CDK4I is absent or its biological activity is reduced (as a result, for example, of a polymorphism in the gene for CDK4I). To this end, the dosage of CDK4I can vary from about 0.1 mg/kg to about 300 mg/kg, preferably from about 0.2 mg/kg to about 200 mg/kg, in one or more dose administrations daily, for one or several days.

B. Gene Therapy

The present invention identifies mutations in a target sequence of CDK4I that are unique to the primary tumor isolated from a subject and metastatic sites derived from the primary tumor. In the tumor cells, the mutated nucleotide sequence is expressed in an altered manner as compared to expression in a normal cell; therefore, it is possible to design appropriate therapeutic (as well as diagnostic) techniques directed to this specific sequence. Thus, where a cell-proliferative disorder is associated with the expression of a particular mutated tumor suppressor gene nucleic acid sequence, a nucleotide sequence that interferes with the specific expression of the mutated gene at the transcriptional or translational level can be used. This approach utilizes, for example, antisense oligonucleotides and/or ribozymes to block transcription or translation of a specific mutated mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). To date, several tumor suppressor genes and oncogenes have been targeted for suppression or down-regulation including, but not limited to, p53 (V. S. Prasolov et al., *Mol. Biol.* (Moscow) 22:1105–1112, 1988); ras (S. K. Anderson et al., *Mol. Immunol.* 26:985–991, 1989; D. Brown et al., Oncogene Res. 4:243–249, 1989); fos (B. Levi et al., *Cell. Differ. Dev.* 25 (Suppl): 95–102, 1988; D. Mercola et al., Gene 72:253–265, 1988); and myc (S. 0. Freytag, *Mol. Cell. Biol.* 8:1614–1624, 1988; E. V. Prochownik et al., *Mol. Cell. Biol.* 8:3683–3695, 1988; S. L. Loke et al., *Curf. Top. Microbiol. Immunol.* 141:282–288, 1988).

It is not sufficient in all cases to block production of the target mutant gene. As described in A. J. Levine, et al., (*Biochimica et Biophisica Acta.*, 1032:119–136, 1990), there are at least five types of mutations that can contribute to the tumor phenotype. Briefly, Type I mutations are those mutations in genes that result in abnormal protein products, which act in a positive dominant fashion. Examples of such mutations are those in H-ras and K-ras genes that result in amino acid changes at positions 12 or 61 in the protein, leading to a protein that binds GTP and is constantly signaling for cell growth. Type II mutations are those that result in overproduction of an oncoprotein, such as the bcr-abI translocation that results in overproduction of a normal myc protein and an altered abi protein. Type III mutations are loss of function mutations wherein tumors arise as the result of loss of both alleles, such as with the retinoblastoma sensitivity gene (Rb) on human chromosome 13q14 and the Wilm's tumor sensitivity gene localized at 11q13. In 75% of colorectal carcinomas, one allele at the p12-p13.3 locus of chromosome 17 containing the p53 gene is commonly deleted, and in some cases the other p53 allele which remains in the colorectal cancer cells has been shown to produce a mutant p53 protein that presumably contributes to tumorigenesis. Type IV mutations are those that result in expression of a protein that does not directly contribute to the growth of cells, but enhances the ability of cancer cells to survive. For instance, mutations to the v-erb-A gene results in erythroblasts transformed with the altered gene being kept in the replication cycle. Type V mutations result from addition of new genetic information into tumor cells, commonly by way of a virus. In some cases the virus integrates its DNA into the cellular genome to produce proteins that bind to cellular negative regulators of growth, such as RB and p53, and thus, in effect, mimic the Type III loss of function mutation mechanism.

Antisense therapy can be used to block production of mutant proteins that act directly to increase the probability of producing neoplastic cells, such as in mechanism Type III, Type IV and Type V mutations that mimic Type III. Antisense is also therapeutically effective when mutation is not dominant, for instance when a non-mutant allele remains that encodes the proper protein. However, when the mutation is dominant, as in Type I mutations, and in cases wherein either both alleles are deleted or one is deleted and the other is mutant, as in certain Type III mutations, antisense therapy is preferably accompanied by replacement therapy. In replacement therapy a wild type gene is introduced into the target cells identified as having a mutant tumor suppressor gene or protooncogene which results in production of the wild type protein necessary to forestall development of the neoplasia associated with the identified mutant gene(s).

In the case of tumor suppressor genes, it is known that introducing a suppressor gene into cultured cells either causes cell death or causes no discernible changes, however, the cells may no longer be tumorigenic in animals. Thus, in cases where ribozyme and/or antisense therapy is accompanied by gene replacement therapy, the chances are increased that the cell population containing the mutant gene for which the ribozyme or antisense oligonucleotide is specific will no longer contribute to development of neoplasia in the subject being treated.

Synthetic antisense oligonucleotides are generally between 15 and 25 bases in length. Assuming random organization of the human genome, statistics suggest that a 17-mer defines a unique sequence in the cellular mRNA in human DNA; a 15-mer defines a unique sequence in the cellular mRNA component. Thus, substantial specificity for a selected genetic target is easily obtained using the synthetic oligomers of this invention.

In the cell, the antisense nucleic acids hybridize to the corresponding mRNA, forming a double-stranded molecule. The antisense nucleic acids, interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nucleotide mutant producing cell. The use of antisense methods to inhibit the in vitro translation of genes is well-known in the art (Marcus-Sakura, *Anal.Biochem.*, 172:289, 1988). Less commonly, antisense molecules which bind directly to the DNA may be used.

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences associated with production of a mutated proto oncogene or tumor suppressor gene in an RNA molecule and cleave it (Cech, *J.Amer.Med. Assnp.*, 260:3030, 1988). A major advantage of this approach is that, because they are sequence-specific, only target mRNAs with particular mutant sequences are inactivated.

There are two basic types of ribozymes, namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species, and 18-based recognition sequences are preferable to shorter recognition sequences.

Unmodified oligodeoxyribonucleotides are readily degraded by serum and cellular nucleases. Therefore, as is well known in the art, certain modifications of the phosphate backbone have conferred nuclease resistance to antisense DNA. For instance phosphorothioate, methylphosphonate, and α-anomeric sugar-phosphate, backbone-modified oligomers have increased resistance to serum and cellular nucleases. In addition, methylphosphonates are nonionic and offer increased lipophilicity to improve uptake through cellular membranes. The use of modified oligonucleotides as antisense agents may require slightly longer or shorter sequences because chemical changes in molecular structure can affect hybridization (L. A. Chrisey et al., *BioPharm*, 4:36–42, 1991). These backbone-modified oligos bind to a target sequence and exert their inhibitory effects by blocking the binding of the cell's translational machinery to a specific RNA or by inducing ribonuclease H activity through the formation of RNA/DNA duplex structures.

The present invention also provides gene therapy for the treatment of cancer conditions; i.e., cell proliferative disorders that are mediated by a deletion of, or polymorphism in, the CDK4I gene. Such therapy would achieve its effect by introduction of the specific antisense polynucleotide and/or replacement wild type gene into cells identified by the methods of this invention as having the proliferative disorder caused by mutated genes. Whether the cell will require replacement of the wild type gene encoding the CDK4I gene as well as antisense therapy to prevent replication of a CDK4I gene bearing a polymorphism must be determined on a case by case basis and will depend upon whether the mutation has a dominant effect, ie., whether both alleles of the wild type gene have been destroyed so that total absence of the gene has a cell proliferative effect.

Delivery of antisense tumor suppressor polynucleotides specific for mutated genes as well as of replacement wild type genes can be achieved using a recombinant expression vector such as a chimeric virus or a colloidal dispersion system. Preferred for therapeutic delivery of antisense sequences is the use of liposomes, especially targeted liposomes.

Various viral vectors that can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting one or more sequences of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the polynucleotides of interest. A separate vector can be utilized for targeted delivery of a replacement gene to the cell(s), if needed, or the antisense oligonucleotide and the replacement gene can optionally be delivered via the same vector since the antisense oligonucleotide is specific only for target gene containing a polymorphism.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, Ψ2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

Another targeted delivery system for antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.24.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Other means for performing gene therapy are known in the art; to wit, Felgner, et al., *Science*, 247:1465, 1990; Stibling, et al., *Proc.Natl.Sci.Acad. USA*, 89:11277–11281, 1992; and, Tang, et al., *Nature*, 356:152–154, 1992, (the disclosures of which are incorporated herein by this reference to illustrate knowledge in the art concerning methods for performing gene therapy). However, the preferred means for performing gene therapy of the invention is the administration of such genes in "naked", non-replicating form (i.e., without association with a viral vector, liposome, host cell or equivalent means for expression of nucleic acids). Further, the preferred routes for administration of such naked nucelotides is via injection into skeletal muscle or, most preferably, via introduction into tissue which contains a relatively high concentration of antigen presenting cells.

X. CDK4I KITS AND PRODUCTS

For use in the diagnostic research and therapeutic applications suggested above, kits are also provided by the invention. In the diagnostic and research applications such kits may include any or all of the following: assay reagents, buffers, CDK4I protein and/or fragments, CDK4I recombinant expression vectors, CDK4I oligonucleotides and other hybridization probes and/or primers, and/or a suitable assay device. A therapeutic product may include sterile saline or another pharmaceutically acceptable emulsion and suspension base for use in reconstituting lyophilized CDK4I or anti-CDK4I suspensions, suitably labeled and approved containers of CDK4I or anti-CDK4I compositions, and kits containing these products for use in connection with the diagnostic kit components as described above.

Such a kit may also comprise a carrier means being compartmentalized to receive in close confinement one or more container means such as vials, tubes, and the like, each of the container means comprising one of the separate elements to be used in the method.

For example, one of the container means may comprise a hybridization probe that is or can be detectably labelled. A second container may comprise a cell lysis buffer. The kit may also have containers holding nucleotide(s) for amplification of the target nucleic acid sequence and/or a container comprising a reporter-means, such as a biotin-binding protein, such as avidin or streptavidin, bound to a reporter molecule, such as an enzymatic, fluorescent, or radionuclide label.

The invention having been fully described, it is further illustrated by the example below. It will be understood, however, that the invention is not limited by the examples but is defined by the appended claims.

EXAMPLE I

IDENTIFICATION AND CHARACTERIZATION OF THE CDK4I GENE

MTAse cDNA (SEQ ID NO: 14) was isolated and used to probe a human placenta lambda phage library. A 2 kilobase Hind III fragment contained the 3'-end of the MTAse gene by sequence analysis. Chromosome walking was performed, starting with the 3'-end of MTAse. Several screening cycles of the known P1 phage (see, e.g., Pierce, et al., *Meth. Enzymol.*, 216:549–574, 1992) and subsequent lambda phage libraries led to the isolation of clones that encompassed the deleted region in T98G. Restriction fragments of these phage were subcloned, partially sequenced, and mapped by Southern blotting and poulsed field gel electrophoresis. FIG. 4 shows the map of human chromosome 9p21 between the MTAP and interferon-$\beta$ (IFNB) gene loci, focusing on the deleted segment in the T98G glioma cell line.

The polymerase chain reaction (PCR) was used to determine the frequency of deletion of several sequence tagged sites (STS) from chromosome 9p in 46 different human malignant cell lines (Table 1). Depending on the cell type, either STS 54F, or STS 5Bs was deleted most frequently. These results focused attention on the 50 kilobase region between STS 54F and STS 5BS.

Eight malignant cell lines with breakpoints between 54F and 5BS were then analyzed by STS-PCR, with new probes from the intervening region. The deletion maps are shown in FIG. 5. A 19 kilobase lambda phage clone (10B1) identified the most frequently deleted site (see, FIG. 4 (*a*)). Phage DNA of clone 10B1 was digested with ECORI and subcloned into ECO-RI-cut pBLUESCRIPT 11 SK+ (Stratagene, La Jolla, Calif.). DNAs from human placenta and melanoma cell lines were digested with EcoRI, resolved on a 0.8% agarose gel, and transferred to nylon membranes. Subclones were subjected to automated DNA sequencing. The 4.2Kb subclone 10B1-10 contained both the CDK4I and the CDK413' nucleotide sequences (SEQ ID NO's 1–2 and 4–5) while the CDK4i5' nucleotide sequence is contained in a 10A1 subclone.

The sequence of the 10B1-10 subclone from clone 10B1 (FIG. 4 (*a*)) contains a 306 base pair open reading frame. The 3'-end of the coding region, and the 3'-noncoding region, are located 2.6 kilobases toward the MTAse gene while the 5'-end of the gene is telomeric to the deleted region in T98G.

The PCR amplification reactions were carried out in a total volume of 20 $\mu$l, containing 0.1 $\mu$g of DNA, 1×PCR buffer (10 mM) Tris-HC1, pH 8.3, 50 mM KC1, 1.5 mM MgC1$_2$, 0.01% gelatin), 200 $\mu$M of each dNTP, 20 ng each of sense and anti-sense primers, and 0.5 units of Taq DNA polymerase. Thirtyfive cycles were performed (64° C. annealing and 72° C. extension) followed by gel electrophoresis.

CDK4I5' (SEQ ID NO: 3) is a 126 bp product generated by reverse transcriptase-PCR in cell line H661 (ATCC Accession No. HTB-183) using a sense primer (5'-AATTCGGCACGAGGCAGCAT-3'; SEQ ID NO: 24) and an anti-sense primer (5'-TTATTTGAGCTTTGGTTCTG-3'; SEQ ID NO: 25). PCR products were subcloned and sequenced. Clone p7–4 (ATCC Accession No. 55540) contained the 5' sequence of the CDK4 inhibitor cDNA. A 139 bp product was amplified from clone p7–4 with a sense primer and a new anti-sense primer (5'-TCGGCC-TCCGACCGTAACTA-3'; SEQ ID NO: 26) and used for Southern blotting. Blots were hybridized at 65° C. overnigh, washed at 65° C. in 0.1×SSC containing 0.1% SDS, and exposed to X-ray film.

EXAMPLE II

DELETION OR POLYMORPHISMS IN THE CDK4I GENE IN CANCER CELL LINES

As shown in FIG. 9, the 46 originally screened malignant cell lines (Table 1) were rescreened with STS-PCR primers, corresponding to the CDK4I' CDK4I' and CDK4I3' CDK4I3' exons (SEQ ID NOS:8–11) (SEQ ID NO.'s 8–11). Sixty-one percent of melanomas, 87% of gliomas, 45% of non-small cell lung cancers, and 64% of leukemias have homozygous deletions of the CDK4I CDK4I gene fragment (Table 1).

Melanoma cell line WM266-4 has deleted only the 5'-end of the CDK4 inhibitor gene (SEQ ID NO. 3). It was positive for CDK4I', negative for STS 5BS, and produced an abnormal 7.0 kilobase band after EcoRI digestion, electrophoresis and hybridization to a probe from the 5'-region of the CDK4 inhibitor gene. On the other hand, melanoma cell line SK-MEL-31 has deleted only the 3'-end of the CDK4I gene (SEQ ID NO. 5). The Detroit 462 cell line (a pharyngeal carcinoma) has a 29 kilobase deletion within the CDK4I gene. It was positive for CDK4I3', negative for CDK4I', but positive for STS-5BS and STS-71F. The latter two STSs are located centromeric to the 5'-end of the CDK4 inhibitor gene.

Reverse transcriptase-polymerase chain reaction (RT-PCR) assays in human cells revealed CDK4 inhibitor gene transcript in normal cells, but not in cancers with established deletions of the CDK4 inhibitor gene (FIG. 9).

To perform the assays, mRNA was purified with a "FAST-TRACK" Kit (Invitrogen, San Diego, Calif.) and was treated with RNase-free DNase I (Pharmacia) using human placenta DNA as a control to ensure complete DNase I digestion. After first-strand cDNA synthesis with a Stratascript RT-PCR Kit (Stratagene La Jolla, Calif.), cDNA was amplified with CDK4I3' primers (58° C. annealing and 70° C. extension).

Primers for the control G3PDH gene (5'-TGGTATGGTGGAAGGACT-CATGAC-3' (SEQ ID NO:27) and 5'-ATGCCAGTGAGCTTCCCGTTCAGC-3' (SEQ ID NO:28)) amplified a 190 bp product (55° C. annealing and 72° C. extension). RT-PCR's for the CDK4I3' axon and G3PDH were performed separately and resolved on a 2% agarose gel. The 355 bp RT-PCR product seen in lanes 1, 2 and 4 of FIG. 9 derived from cDNA. These results indicate that human cells contain a single CDK4 inhibitor gene, that is homozygously deleted or rearranged in the majority of melanomas, gliomas, and leukemias, and in many non-small cell lung cancers.

EXAMPLE III

DETECTION OF A DELETION OF THE CDK4I GENE

A. Preparation of Solid Support Materials for PCR-ELISA

Twenty $\mu$l of 2.5 pmol/$\mu$l an aminated oligonucleotides specific for the CDK4I gene in 5 mM 2-[N-morpholino] ehthanesulfonic acid and 1 mM EDTA, pH. 5.5 were placed in each well of a 96 well microtiter plate made of polycarbonate (Costar, Cambridge, Mass.). Then 20 $\mu$l of 4 mg/ml 1-ethyl-3-(3-dimethylaminopropyl) carbodiimide hydrochloride (EDC, Pierce Chemical) were added and the plate was incubated at 37° C. for 2 hours. Wells were then washed once with phosphate buffered saline (PBS) and blocked with 1% bovine serum albumin (BSA) for one hour.

B. Trible Primer PCR Amplification

Using the primers described in SEQ ID NO's: 8–13, genomic DNA obtained from the cell lines identified in Table 1, supra, was amplified as follows. 0.1 $\mu$g of genomic DNA was added to an amplification mixture consisting of 10 mM Tris-HCl, pH 8.3, 50 mM KCl, 1.5 mM MgCl$_2$, and 0.01% gelatin (PCR buffer), as well as 200 $\mu$M of each dNTP, 20 ng each of the primers, and 0.5 units of Taq DNA polymerase. Thirty cycles were performed in a Perkin-Elmer Cetus DNA thermal cycler, each cycle consisting of denaturation (94° C., 1 minute), annealing (50–55° C., 1 minute) and extension (72° C., 1 minute).

C. Detection of Hybridization and Extension of Immobilized Primers

The wells were washed three times with HW buffer (3×SSC, 0.1% N-lauroylsarcosine) and once with blocking buffer (0.5% GENIUS blocking reagant (a trademarked product of Boehringer Mannheim), in 100 mM Tris-HCl, pH 7.5, and 800 mM NaCl), and incubated with 80 $\mu$l of tetramethylbenzidine and horseradish peroxidase (kikegaard & Perry Laboratories). The reaction was stopped with 80 $\mu$l of 1M 0-phosphate at the appropriate time point. 150 $\mu$l each was transferred to another microtiter plate and OD was measured at 450 nm with a microtiter reader from Molecular Devices, Menlo Park, Calif.

The results of this assay are summarized in Table 1, supra.

EXAMPLE V

DETECTION OF A GERMLINE NONSENSE MUTATION IN DYSPLASTIC NEVUS SYNDROME CELLS

Primers for CDK4I' (SEQ ID NO's: 8–9) were constructed and the reverse transcriptase polymerase chain reaction (RT-PCR) used to amplify a CDK4I gene transcript in a human lymphoblastoid cell line (GM06921; derived from a human patient with dysplastic nevus syndrome (familial melanoma). Using the technique described by Orita, et al., supra, and/or the technique described by Wu, et al., supra, a mutated form of the CDK4I gene transcript was identified in the GM06921 cell line). Sequence analysis of the transcript revealed a C to T transition at position 166 of the mRNA, which results in a nonsense mutation (s FIG. 6).

EXAMPLE VI

DETECTION OF A CDK4I5' GENE MICRODELETION IN A LEUKEMIA CELL LINE

Primers for CDK4I5' (SEQ ID NO's: 12–13) were constructed and the reverse transcriptase polymerase chain reaction (RT-PCR) used to amplify a CDK4I gene transcript in a human leukemia cell line, U937 (ATCC Accession No. CRL 1593). Using the technique described by Orita, et al., supra, and/or the technique described by Wu, et al., supra, a mutated form of the CDK4I5' gene transcript was identified in the U937 cell line and sequenced, showing a microdeletion of 18 base pairs (see, FIG. 7).

SUMMARY OF SEQUENCES

SEQ ID NO: 1 is the nucleotide sequence for the 5' region of human genomic CDK4I and includes the exon sequence for the 5' region of CDK4I.

SEQ ID NO. 2 is the nucleotide sequence for the internal and 3' regions of human, genomic CDK4I.

SEQ ID NO's: 3 through 5 are, respectively, the CDKI5', CDK4I', and CDK4I3' exons.

SEQ ID NO's: 6 and 7 are sequences for oligonucleotide primers for the region between 54F and 5BS of the 9p21 chromosome (i.e., corresponding to clone 10B1).

SEQ ID NO's: 8 through 13 are sequences for oligonucleotide primers for the CDK4I', CDK4I3'and CDK4I5' exons, respectively.

SEQ ID NO: 14 is the full-length genomic nucleotide sequence for MTAse.

What is claimed is:

1. An isolated polypeptide comprising a cyclin dependent kinase 4 inhibitor (CDK4I) or biologically active fragment thereof, wherein said CDK4I is encoded by a DNA molecule consisting of SEQ ID NO: 3, 4, and 5 in order 5' to 3'.

2. A pharmaceutical composition comprising a substantially pure polypeptide of claim 1.

3. The isolated polypeptide of claim 1, wherein the polypeptide comprises CDK4I.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
        (A) LENGTH: 1146 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..1146
        (D) OTHER INFORMATION: /note= "5' region of human genomic
           CDK4I"

(ix) FEATURE:
        (A) NAME/KEY: exon
        (B) LOCATION: 390..515
        (D) OTHER INFORMATION: /note= "CDK4I5' exon"

(xi) SEQUENCE DESCRIPTION: SEQ ID NO: 1:

```
TTTGGGGNNA AGTTTGGGAA AANCCAATCC TCCTTCCTTT CCAACNNTGC TTCTGGCGAG      60

GCTCCTTCCC GGCTTGTTCC CCCNGGGGGA AGACCCAACC TGGGCCGACC TTCAGGGTTC     120

CCACATTCCC TAANTGCTCG GAGTTAATAN CACCTCCTCC GAGNACTCGC TCACGNCGTC     180

CCCTTNCCTG GAAAGATACC GCGNTCCCTC NAGAGGATTT GAGGGACAGG GTCGGAGGGG     240

NCTCTTCCGC CAGCACCGGA GGAAGAAAGA GGAGGGGCTG GCTGGTCACC AGAGGGTGGG     300

GCGGACCGCG TGCGCTCGGC GTCTGCGGAG AGGGGGAGAG CAGGCAGCGG GCGGCGGGGA     360

GCAGCATGGA GCCGGCGGCG GGGAGCAGCA TGGAGCCTTC GGCTGACTGG CTGGCCACGG     420

CCGCGGCCCG GGGTCGGGTA GAGGAGGTGC GGGCGCTGCT GGAGGCGGGG GCGCTGCCCA     480

ACGCACCGAA TAGTTACGGT CGGAGGCCGA TCCAGGTGGG TAGAGGGTCT GCAGCGGGAG     540

CAGGGGATGG CGGGCGACTC TGGAGGACGA AGTTTGCAGG GGAATTGGAA TCAGGTAGCG     600

CTTCGATTCT CCGGAAAAAG GGGAGGCTTC CTGGGGAGTT TTCAGAAGGG GTTTGTAATC     660

ACAGACCTCC TCCTGGCGAC GCCCTGGGGG CTTGGGAAGC CAAGGAAGAG GAATNAGGAG     720

CCACGCGCGT ACAGATCTCT CGAATGCTGA SAMGATYTTR AGGGSSGRAM ATATTTGTAT     780

TCAGATGGAA GTATKCTCTT TATCAGATAC AAAATTTACG AACGTTTGGG ATAAAAAGGG     840

AGTCTTAAAG AAATKTAAGA TGTKCTGGGA CTACTTAGCC TCCAATTCAC AGATACCTGG     900

ATGGAGCTTA TCTTTCTTAC TAGGAGGGAT TATCAGTGGA AATCTGTGGN GTATGTTGGA     960

ATAAATATCG AATATAAATT TTGATCGAAA TTATTCAGAA GCGGCCGGGC GCGGTGCCTC    1020

ACGCCTTGTA ATCCCTTCAC TTTGGGAGAT CAAGGCGGGG GGGAATCANC TGAGGTCGGG    1080

AGTTCGAGAA CAGCCTGGGC AACAGGTGAA AACCTCGCCT CCTACTAAAA AATACAAAAA    1140
```

GTAGNC                                                                                          1146

(2) INFORMATION FOR SEQ ID NO: 2:

(i) SEQUENCE CHARACTERISTICS:
        (A) LENGTH: 4286 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..4286
        (D) OTHER INFORMATION: /note= "internal and 3' regions of
            human genomic CDK4I"

(ix) FEATURE:
        (A) NAME/KEY: exon
        (B) LOCATION: 192..497
        (D) OTHER INFORMATION: /note= "CDK4I' exon"

(ix) FEATURE:
        (A) NAME/KEY: exon
        (B) LOCATION: 3157..3171
        (D) OTHER INFORMATION: /note= "CDK4I3' exon"

(xi) SEQUENCE DESCRIPTION: SEQ ID NO: 2:

```
GAATTCATTG TGTACTGAAG AATGGATAGA GAACTCAAGA AGGAAATTGG AAACTGGAAG      60

CAAATGTAGG GGTAATTAGA CACCTGGGGC TTGTGTGGGG GTCTGCTTGG CGGTGAGGGG     120

GCTCTACACA AGCTTCCTTT CCGTCATGCC GGCCCCCACC CTGGCTCTGA CCATTCTGTT     180

CTCTCTGGCA GGTCATGATG ATGGGCAGCG CCCGAGTGGC GGAGCTGCTG CTGCTCCACG     240

GCGCGGAGCC CAACTGTGCC GACCCCGNCA CTCTCACCCG ACCCGTGCAC GACGCTGCCC     300

GGGAGGGCTT CCTGGACACG CTGGTGGTGC TGCACCGGGC CGGGGCGCGG CTGGACGTGC     360

GCGATGCCTG GGGCCGTCTG CCCGTGGACC TGGCTGAGGA GCTGGGCCAT CGNGATGTCG     420

CACGGTACCT GCGCGCGGCT GCGGGGGGCA CCAGAGGCAG TAACCATNCC CGNATAGATG     480

CCGCGGAAGG TCCCTCAGGT GAGGACTGAT GATCTNAGAA TTTGNCCCCT GAGAGCTTCC     540

AAAGCTCAGA GNATTCATTT TCCAGCACAG AAAGTNCAGC CCGGGAGANC AGTCTCCGGT     600

CTTGTCTCAG CTCACGCGCC AATCGGTGGG ACGGCCTGAG TCTCCCTATC GCCCTGCCCC     660

GCCAGGGCGG CAAATGGGAA ATAATCCCGA AATGGACTTG CGCACGTGAA AGCCCATTTT     720

GTACATTATA CTTCCCAAAG CATACCACCA CCCAAACACC TACCCTCTGC TAGTTCAAGG     780

CCTAGACTGC GGAGCAATGA AGACTCAAGA GGCTAGAGGT CTAGTGCCCC CTCTTCCTCC     840

AAACTAGGGC CAGTTGCATC CACTTACCAG GTCTGTTTCC TCATTTGCAT ACCAAGCTGG     900

CTGGACCAAC CTCAGGATTT CCAAACCCAA TTGTGCGTGG CATCATCTGG AGATCTCTCG     960

ATCTCGGCTC TTCTGCACAA CTCAACTAAT CTGAACCTCC TCAGCTAATC TGACCCTCCG    1020

CTTNATGCGG TAGAGTTTAC CAGAGCTGCC CCAGGGGGTT CTGGGACAT CAGGACCAAG    1080

ACTTCGCTGA CCCTGGCAGT CTGTGCACCG GAGTTGGCTC CTTTCCCTCT TAAACTTGTG    1140

CAAGAGATCG CTGAGAGATG AAGGTAGAAT TATGGTCCTC CTTGCCCTNG CCTTTCCTTT    1200

TAGTGATCTC AAAGCATCCT CCCTCCGTCC CCATTCCATG GCCCCAGTTC ACTACTCCCA    1260

CAGCTGTCTG GTGAAACTGA CAACATTACT CAATTGTTTC TGGGGGAGG AACATTTTTT    1320

TTTGAAACAA AATAGATATA TGAAACAGTA CACGGGAATT AACACGATTA TTTAAGGTAA    1380

AACATGACCT TGAAGATTAT GAAATCCATC TTATTTTGGC CCAGAACGGG GGCATTGGKC    1440
```

```
-continued

TCCTTGGCCC ATAGGGGAGC TGGGGAGGAC AGGGTGAAGA GTTAGCTCTA AGCCCTCTNN    1500

TTGGAGATGC TGTAAATACA GAACGCAAAA TCACCTTCGA AGTTAAAGAC GCGAAGTTCT    1560

TCTTTACTCG GCCCCTCCTC CCCTCCCCCC CGACAATTCC CTCCAGTTAC AGCTAGCATC    1620

CAGGTCCCGG GAGGTGAAGA AGGAGACTTC GGCTCCAGTT ACAGCTAGCA TCCGGGTCCC    1680

GATTTAGAAG GAGCTGCCAA TTACAGCGCG GTTCCAGGGC TGAGCAAAAA GCCTGAGGAG    1740

CCAAGTGGGA GAGGGAGTAA AACTACTGAA TTGGGCCACA AGCAAATGAA TAAACTGAAC    1800

GACTCTTAAC CAAACCTAAT ATATTTAATC CAAACACACA AGTCTTTCAT TTCTTCCCTC    1860

CTCCCTTCCT TCTCTTACTC CCCAACACCC CCTCTTCAAG CACAATTAAT TATATGGTTA    1920

GATTCTACTG CGTGATCAGC CCTGTTCTAG GTGGTGGGCA CGCCAAGGTG AATGAGACCA    1980

AACAAGAGTC TTGCCCTCAT GGGGTTTACA TTTGGAGACA GAGTCGATCT GTTGCCCAAC    2040

CTGGAGTGCA GTGGCGCGAT CACAGCTCAC TGCAGCCTCA AACTCCCTGG CTCAAGGGGT    2100

TCTCCCACCT GAGCCTCCCG ACTAGCTGGG ACCACAGGTG CACGCCACGA CGCCTGGGTT    2160

TGTTTGTTTG TTTAATAGAG ACGAAGGTCT CACCATGTTA TCTGGGCTCA AGCGATCATC    2220

CCCCCTCCTC CTCCTAAAGT ACTGGGATTA CAGTCCCAAG CTATCTTGCC CGACCTGGGA    2280

AACAGACGTT AAGGAAGATA ACAATCTATT TTCAGAGAGC GAGTTTATAA AACCAATGCA    2340

ATGGGTAAAT ATGAAGTGTG AATAGGAGGA GAAGCTAAAG AGTGGTCGGA GAATCTAATG    2400

CAAGCTACGG GAGAAAGAAA CTCAAGTGCA AATGCTGCCT CAGGAATAAA CGTAAAAAGA    2460

GACTTTCAAG TGCAAATGCT CCCTCAGGAA TAAAATAATC TTGAGACTCT CAAGTGTAAA    2520

TGCTGCCTCG GGAGAACCGA ACGGCGAGCT GGAGCCCATA CGCAACGAGA TTAGAGAGGA    2580

AGGCAGAAGC CAGAGCACAT GAATAAATGA GCATCCATTT TGTTTCAGAA ATGATCGGAA    2640

ACCATTTGTG GGTTTGTAGA AGCAGGCATG CGTAGGGAAG CTACGGGATT CCGCCGAGGA    2700

GCGCCAGAGC CTGAGGCGCC CTTTGGTTAT CGCAAGCTGG CTGGCTCACT CCGCACCAGG    2760

TGCAAAAGAT GCCTGGGGAT GCGGGAAGGG AAAGGCCACA TCTTCACGCC TTCGCGCCTG    2820

GCATTGTGAG CAACCACTGA GACTCATTAT ATAACACTCG TTTTCTTCTT GCAACCCTGC    2880

GGGCCGCGCG GTCGCGCTTT CTCTGCCCTC CGCCGGGTGG ACCTGGAGCG CTTGAGCGGT    2940

CGGCGCGCCT GGAGCAGCCA GGCGGGCAGT GGACTAGCTG CTGGACCAGG GAGGTGTGGG    3000

AGAGCGGTGG CGGCGGGTAC ATGCACGTGA AGCCATTGCG AGAACTTTAT CCATAAGTAT    3060

TTCAATGCCG GTAGGGACGG CAAGAGAGGA GGGCGGGATG TTCCACACAT CTTTGACCTC    3120

AGGTTTCTAA CGCCTGTTTT CTTTCTGCCC TCTGCAGACA TCCCCGATTG AAAGAACCAG    3180

AGAGGCTCTG AGAAACCTCC GGAAACTTAG ATCATCAGTC ACCGAAGGTC CTACAGGGCC    3240

ACAACTGCCC CCGCCACAAC CCACCCCGCT TTCGTAGTTT TCATTTAGAA AATAGAGCTT    3300

TTAAAAATGT CCTGCCTTTT AACGTAGATA TATGCCTTCC CCCACTACCG TAAATGTCCA    3360

TTTATATCAT TTTTTATATA TTCTTATAAA AATGTAAAAA AGAAAACAC CGCTTCTGCC    3420

TTTTCACTGT GTTGGAGTTT TCTGGAGTGA GCACTCACGC CCTAAGCGCA CATTCATGTG    3480

GGCATTTCTT GCGAGCCTCG CAGCCTCCGG AAGCTGTCGA CTTCATGACA AGCATTTTGT    3540

GAACTAGGGA AGCTCAGGGG GGTTACTGGC TTCTCTTGAG TCACACTGCT AGCAAATGGC    3600

AGAACCAAAG CTCAAATAAA AATAAAATAA TTTTCATTCA TTCACTCATT TATTGTCAAC    3660

ATTTATTGAG CACCTATTAC AACAATTTCA TCGCATGGAA GACAGCATCG TTTCTGACAC    3720

TGTTGTTTCA TGTATCTCTT AGAAAACGC TGCTATTAGA CATCTAACAC TATTTATCTT    3780

GAGGTGATAA AATATCAAAA GCCGTGTCTC AAGATCGATG AAATGCGGTT AAAATGATGA    3840
```

| ATAGAAACTC TAGGGGGACC TCATATCGAT AGACTCGAGA CTGGCACATC TGGAGATCCG | 3900 |
| TATTTATCCG GCTTCCCCTT CCAGATCACG CGAGGTTTGG GATATTTTGC TCACCAGGCC | 3960 |
| TCAGCCAGGT AACTGAATCC AGCCAACCCT GGCCCATAGT CTCGGAATCC GACTCGGCTC | 4020 |
| CCAGTCCCCG CCTCGGCGTT CTGAGACCCC CAGGCTGGGT TCCAAGAGGG CTGTGAGGTT | 4080 |
| GCGAATGACT GCTGCCAAAC CGGAAGGAAC TCTGCGGTTC TCTGCCACAG TGGGATTGTT | 4140 |
| GCAGGCACGC GGCTCAGACT TCACTGAGGT TGGGAGATGC TCCTGTCCAC GCTGCCTCAT | 4200 |
| CCCGTGCTGG AGCACTGCAC CTCTATTTTT TTTTTTAGGG TACACGCCAC ATAACATAAA | 4260 |
| ACTAAAAATT TTAAAGAGTA GAATTC | 4286 |

(2) INFORMATION FOR SEQ ID NO: 3:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..126
        (D) OTHER INFORMATION: /note= "CDK4I5' exon"

(xi) SEQUENCE DESCRIPTION: SEQ ID NO: 3:

| ATGGAGCCTT CGGCTGACTG GCTGGCCACG GCCGCGGCCC GGGGTCGGGT AGAGGAGGTG | 60 |
| CGGGCGCTGC TGGAGGCGGG GGCGCTGCCC AACGCACCGA ATAGTTACGG TCGGAGGCCG | 120 |
| ATCCAG | 126 |

(2) INFORMATION FOR SEQ ID NO: 4:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..306
        (D) OTHER INFORMATION: /note= "CDK4I' exon"

(xi) SEQUENCE DESCRIPTION: SEQ ID NO: 4:

| GTCATGATGA TGGGCAGCGC CCGAGTGGCG GAGCTGCTGC TGCTCCACGG CGCGGAGCCC | 60 |
| AACTGTGCCG ACCCCGNCAC TCTCACCCGA CCCGTGCACG ACGCTGCCCG GGAGGGCTTC | 120 |
| CTGGACACGC TGGTGGTGCT GCACCGGGCC GGGGCGCGGC TGGACGTGCG CGATGCCTGG | 180 |
| GGCCGTCTGC CCGTGGACCT GGCTGAGGAG CTGGGCCATC GNGATGTCGC ACGGTACCTG | 240 |
| CGCGCGGCTG CGGGGGGCAC CAGAGGCAGT AACCATNCCC GNATAGATGC CGCGGAAGGT | 300 |
| CCCTCA | 306 |

(2) INFORMATION FOR SEQ ID NO: 5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear

```
    (ii) MOLECULE TYPE: DNA (genomic)

(ix) FEATURE:
        (A) NAME/KEY: exon
        (B) LOCATION: 1..15
        (D) OTHER INFORMATION: /note= "CDK4I3' exon"

(xi) SEQUENCE DESCRIPTION: SEQ ID NO: 5:

GACATCCCCG ATTGA                                                   15

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "CDK4I' primer"

(xi) SEQUENCE DESCRIPTION: SEQ ID NO: 6:

GGAAATTGGA AACTGGAAGC                                              20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "CDK4I' primer"

(xi) SEQUENCE DESCRIPTION: SEQ ID NO: 7:

CAGGTCATGA TGATGGGCAG                                              20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "CDK4I3' primer"

(xi) SEQUENCE DESCRIPTION: SEQ ID NO: 8:

CCCGCTTTCG TAGTTTTCAT                                              20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
```

```
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note= "CDK4I3' primer"

(xi) SEQUENCE DESCRIPTION: SEQ ID NO: 9:

CAGAACCAAA GCTCAAATAA                                            20

(2) INFORMATION FOR SEQ ID NO: 10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note= "5BS primer"

(xi) SEQUENCE DESCRIPTION: SEQ ID NO: 10:

GCTTAGTTTT AGAGGGTGAT                                            20

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note= "5BS primer"

(xi) SEQUENCE DESCRIPTION: SEQ ID NO: 11:

CATCACTCAT AAGAACTGCT                                            20

(2) INFORMATION FOR SEQ ID NO: 12:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..19
            (D) OTHER INFORMATION: /note= "CDK4I5' primer (sense)"

(xi) SEQUENCE DESCRIPTION: SEQ ID NO: 12:

ACCATGGAGC CTTGGCTGA                                             19

(2) INFORMATION FOR SEQ ID NO: 13:

(i) SEQUENCE CHARACTERISTICS:
            (A) LENGTH: 19 base pairs
            (B) TYPE: nucleic acid
```

```
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "CDK4I5' primer (antisense)"

(xi) SEQUENCE DESCRIPTION: SEQ ID NO: 13:

CAATAGTTAC GGTCGGAGG                                                    19

(2) INFORMATION FOR SEQ ID NO: 14:

(i) SEQUENCE CHARACTERISTICS:
        (A) LENGTH: 2763 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..2763
        (D) OTHER INFORMATION: /note= "full-length
            methylthioadenosine phosphorylase (MTAse) genomic
            nucleotide sequence"

(ix) FEATURE:
        (A) NAME/KEY: exon
        (B) LOCATION: 254..421

(ix) FEATURE:
        (A) NAME/KEY: exon
        (B) LOCATION: 616..720

(ix) FEATURE:
        (A) NAME/KEY: exon
        (B) LOCATION: 964..1203

(xi) SEQUENCE DESCRIPTION: SEQ ID NO: 14:

TTTATACAGA GCATGACAGT GGGGTCCTCA CTAGGGTCTG TCTGCCACTC TACATATTTG          60

AAACAGGAGT GGCTTCTCAG AATCCAGTGA ACCTAAATTT TAGTTTTAGT TGCTCACTGG         120

ACTGGGTTCT AGGAGACCCC CTGTGTTAGT CTGTGGTCAT TGCTAGSAGA ATCACTTAAT         180

TTTTTCTAGA CTCTAGGAGA AAACAGTTGG TGGTGTACTC ATCACGGGTT AACAATTTCT         240

TCTCTCCTTC CATAGGCATG GAAGGCAGCA CACCATCATG CCTTCAAAGG TCAACTACCA         300

GGCGAACATC TGGGCTTTGA AGGAAGAGGG CTGTACACAT GTCATAGTGA CCACAGCTTG         360

TGGCTCCTTG AGGGAGGAGA TTCAGCCCGG CGATATTGTC ATTATTGATC AGTTCATTGA         420

CANNNNNNNN NNNNNNNNNN GAGGTCGACG GTATCGATAA GCTTTGTAAA CAATTGTCTT         480

TAGCTTATCC AGAGGAATTG AGTCTGGAGT AAAGACCCAA ATATTGACCT AGATAAAGTT         540

GACTCACCAG CCCTCGGAGG ATGGAAAGAT GGCCTTAAAA TAAAACAAAC AAAAACCTTT         600

TTTGCTTTAT TTTGTAGGAC CACTATGAGA CCTCAGTCCT TCTATGATGG AAGTCATTCT         660

TGTGCCAGAG GAGTGTGCCA TATTCCAATG GCTGAGCCGT TTTGCCCCAA AACGAGAGAG         720

GTGTGTAGTC TTTCTGGAAG GTGTACCAGA ATAAATCATG TGGGCTTGGG GTGGCATCTG         780

GCATTTGGTT AATTGGCAGA CGGAGTGGCC CCATACCCTC ACTCAAGTTT GCTTTGTATT         840

ATGCAAGTTT ATGGAGAGTT ATTTCCTGTT GCTAATAATT TNNNNNNNNN NNNNNNNNNN         900

AAGTGCAGCC TTAAGTTGTG CATGTGCTAG TATGTTTTGA AGTTTCTGGT TTTTCTTTTC         960

TAGGTTCTTA TAGAGACTGC TAAGAAGCTA GGACTCCGGT GCCACTCAAA GGGGACAATG        1020
```

```
GTCACAATCG AGGGACCTCG TTTTAGCTCC CGGGCAGAAA GCTTCATGTT CCGCACCTGG      1080

GGGGCGGATG TTATCAACAT GACCACAGTT CCAGAGGTGG TTCTTGCTAA GGAGGCTGGA      1140

ATTTGTTACG CAAGTATCGC CATGGGCACA GATTATGACT GCTGGAAGGA GCACGAGGAA      1200

GCAGTAGGTG GAATTCTTTT CTAAGCACAT ATAGCATGGG TTTCTGGGTG CCAATAGGGT      1260

GTCTTAACTG TTTGTTTCTA TTACGTTAGT TTCAGAAAGT GCCTTTCTAC AAGGTTTTGA      1320

AGTTGTTAAT ATTTTCTGTA GTTCCATTGG AAGGTAAGAA CAAAGATCAA AGAAAGAAA      1380

GAGACACTTT TACCCAAGGA TCAGTAGTGA AAATAGTACA TTGTAGGCAT GTAGATGTGT      1440

TGAGAATCAT ACTAAGACTT GGGCCTTANN NNNNNNNNNN NNNNNNNNNN NNTACCCTAC      1500

ATTGAGGATT CGGTTTCAGC AGATAAATTT GAGGACACA AACATTTAGG CTGTAGCAAG       1560

GCTGGAGCTC AGAAAAATGT TTTATGACAA GCAGTGGAAT TTTAAGTTCT AGTAACCTCC      1620

AGTGCTATTG TTTCTCTAGG TTTCGGTGGA CCGGGTCTTA AGACCCTGA AGAAAACGC        1680

TAATAAAGCC AAAAGCTTAC TGCTCACTAC CATACCTCAG ATAGGGTCCA CAGAATGGTC      1740

AGAAACCCTC CATAACCTGA AGGTAAGTGC AGCCATGGAC AATCAGGCAT GTCTGTAGAC      1800

TCTCTATTGT CTTCTTTTCT TACTTGCATT TCACCTTTGG TCCTCATGTA TTTTTTGCCA      1860

GCCTAGATGT TTTCAACAAG TTTTTGTGAC ATCTACTACT ACCATACCAA CCACTTGTGA      1920

AACTGAGTAG TCTTATTTTC TTGGCTGGTA GTGCAGANNN NNNNNNNNNN NNAATAAACA      1980

ATAATCCAGG CTGGGCTGGT ATGGCAATAA GTGATTATCA GAACAATGCT CTGAGATAAG      2040

CATTATTAAC CTCACTTTAC AGGAAAGGGA GGTGAGGAAC CAAGAGTTTA GAGTACCCGA      2100

AGTTCCACAT CTGGTTAGTG AACTTGAAAA TTTTCTGTAG AATTTATTTA AAGTGTATGT      2160

TTCCTGCGTC CTCACTTTGA TCTAGAAAAT CAAAATCTGT TTTTTTTTTT AACAAACATC      2220

TCAGTAATTA CGCCAACATG TGAATATCAC TGCCTCCTTT CTTCCTTTCA GAATATGGCC      2280

CAGTTTTCTG TTTTATTACC AAGACATTAA AGTAGCATGG CTGCCCAGGA GAAAAGAAGA      2340

CATTCTAATT CCAGTCATTT TGGGAATTCC TGCTTAACTT GAAAAAAATA TGGGAAAGAC      2400

ATGCAGCTTT CATGCCCTTG CCTATCAAAG AGTATGTTGT AAGAAAGACA AGACATTGTG      2460

TGTATAGAGA CTCCTCAATG ATTTAGACAA CTTCAAAATA CAGAAGAAAA GCAAATGACT      2520

AGTAACATGT GGGAAAAAAT ATTACATTTT AAGGGGAAA AAAACCCCA CCATTCTCTT        2580

CTCCCCCTAT TAAATTTGCA ACAATAAAGG GTGGAGGGTA ATCTCTACTT TCCTATACTG      2640

CCAAAGAATG TGAGGAAGAA ATGGGACTCT TTGGTTATTT ATTGATGCGA CTGTAAATTG      2700

GTACAGTATT TCTGGAGGGC AATTTGGTAA AATGCATCAA AAGACTTAAA AATACGGACG      2760

TAC                                                                   2763

(2) INFORMATION FOR SEQ ID NO: 15:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CGGCACGAGG CAGCATGGAG CCTTCGGCTG ACTGGCTGGC CACGGCCGCG GCCCGGGGTC       60

GGGTAGAGGA GGTGCGGGCG CTGCTGGAGG CGGTGGCGCT GCCCAACGCA CCGAATAGTT      120

ACGGTCGGAG GCCGATCCAG GT                                              142
```

(2) INFORMATION FOR SEQ ID NO: 16:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
CGGCGGGGAG CAGCATGGAG CCTTCGGCTG ACTGGCTGGC CACGGCCGCG GCCCGGGGTC      60

GGGTAGAGGA GGTGCGGGCG CTGCTGGAGG CGGGGGCGCT GCCCAACGCA CCGAATAGTT     120

ACGGTCGGAG GCCGATCCAG GT                                             142
```

(2) INFORMATION FOR SEQ ID NO: 17:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
CAGGTCATGA TGATGGGCAG CGCCCGAGTG GCGGAGCTGC TGCTGCTCCA CGGCGCGGAG      60

CCCAACTGTG NCGACCCCGN CACTCTCACC CGACCCGTGC ACGACGCTGC CCGGGAGGGC     120

TTCCTGGACA CGCTGGTGGT GCTGNANCGG GCCGGGCGC GGGTGGACGT NCGCGAATNC     180

CTGGGGNCGT CTTTCCGTNG ACCTGGNTTN ANGAGCTTGG NCATCGNGAA TNTCGNACGG     240

TACCTNCCCG CNGTTNGGGG GGGACANAGG NAGGAACNAT NCCC                      284
```

(2) INFORMATION FOR SEQ ID NO: 18:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
CAGGTCATGA TGATGGGCAG CGCCCGAGTG GCGGAGCTGC TGCTGCTCCA CGGCGCGGAG      60

CCCAACTGCG CCGACCCCGC CACTCTCACC CGACCCGTGC ACGACGCTGC CCGGGAGGGC     120

TTCCTGGACA CGCTGGTGGT GCTGCACCGG GCCGGGCGC GGCTGGACGT GCGCGATGCC     180

TGGGGCCGTC TGCCCGTGGA CCTGGCTGAG GAGCTGGGCC ATCGCGATGT CGCACGGTAC     240

CTGCGCGCGG CTGCGGGGGG CACCAGAGGC AGTAACCATG CCC                      283
```

(2) INFORMATION FOR SEQ ID NO: 19:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
GATGATGGGC AGCGCCTGAG TGGCGGAGCT GCTGCTGCTC CACGGCGCGG AGCCCAAC         58
```

(2) INFORMATION FOR SEQ ID NO: 20:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
GATGATGGGC AGCGCCCGAG TGGCGGAGCT GCTGCTGCTC CACGGCGCGG AGCCCAAC         58
```

(2) INFORMATION FOR SEQ ID NO: 21:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
AATTCGGCAC GAGGCAGCAT GGAGCCTTCG GCTGACTGGC TGGCCACGGC CGCGGCCCGG        60

GGTCGGGTAG AGGAGGTGCG GGCGCTGCCC AACGCACCGA ATAGTTACGG TCGGAGGC        118
```

(2) INFORMATION FOR SEQ ID NO: 22:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
AATTCGGCAC GAGGCAGCAT GGAGCCTTCG GCTGACTGGC TGGCCACGGC CGCGGCCCGG        60

GGTCGGGTAG AGGAGGTGCG GGCGCTGCTG GAGGCGGTGG CGCTGCCCAA CGCACCGAAT      120

AGTTACGGTC GGAGGC                                                      136
```

(2) INFORMATION FOR SEQ ID NO: 23:

(i) SEQUENCE CHARACTERISTICS:
        (A) LENGTH: 1450 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..1450
        (D) OTHER INFORMATION: /note= "methylthioadenosine
            phosphorylase (MTAse) genomic nucleotide
            sequence"

(ix) FEATURE:
        (A) NAME/KEY: exon
        (B) LOCATION: 254..421

(ix) FEATURE:
        (A) NAME/KEY: exon
        (B) LOCATION: 616..720

(ix) FEATURE:
        (A) NAME/KEY: exon
        (B) LOCATION: 964..1203

(xi) SEQUENCE DESCRIPTION: SEQ ID NO: 23:

| | | | | | |
|---|---|---|---|---|---|
|TTTATACAGA|GCATGACAGT|GGGGTCCTCA|CTAGGGTCTG|TCTGCCACTC|TACATATTTG    60|
|AAACAGGAGT|GGCTTCTCAG|AATCCAGTGA|ACCTAAATTT|TAGTTTTAGT|TGCTCACTGG   120|
|ACTGGGTTCT|AGGAGACCCC|CTGTGTTAGT|CTGTGGTCAT|TGCTAGSAGA|ATCACTTAAT   180|
|TTTTTCTAGA|CTCTAGGAGA|AAACAGTTGG|TGGTGTACTC|ATCACGGGTT|AACAATTTCT   240|
|TCTCTCCTTC|CATAGGCATG|GAAGGCAGCA|CACCATCATG|CCTTCAAAGG|TCAACTACCA   300|
|GGCGAACATC|TGGGCTTTGA|AGGAAGAGGG|CTGTACACAT|GTCATAGTGA|CCACAGCTTG   360|
|TGGCTCCTTG|AGGGAGGAGA|TTCAGCCCGG|CGATATTGTC|ATTATTGATC|AGTTCATTGA   420|
|CANNNNNNNN|NNNNNNNNNN|GAGGTCGACG|GTATCGATAA|GCTTTGTAAA|CAATTGTCTT   480|
|TAGCTTATCC|AGAGGAATTG|AGTCTGGAGT|AAAGACCCAA|ATATTGACCT|AGATAAAGTT   540|
|GACTCACCAG|CCCTCGGAGG|ATGGAAAGAT|GGCCTTAAAA|TAAAACAAAC|AAAAACCTTT   600|
|TTTGCTTTAT|TTTGTAGGAC|CACTATGAGA|CCTCAGTCCT|TCTATGATGG|AAGTCATTCT   660|
|TGTGCCAGAG|GAGTGTGCCA|TATTCCAATG|GCTGAGCCGT|TTTGCCCCAA|AACGAGAGAG   720|
|GTGTGTAGTC|TTTCTGGAAG|GTGTACCAGA|ATAAATCATG|TGGGCTTGGG|GTGGCATCTG   780|
|GCATTTGGTT|AATTGGCAGA|CGGAGTGGCC|CCATACCCTC|ACTCAAGTTT|GCTTTGTATT   840|
|ATGCAAGTTT|ATGGAGAGTT|ATTTCCTGTT|GCTAATAATT|TNNNNNNNNN|NNNNNNNNNN   900|
|AAGTGCAGCC|TTAAGTTGTG|CATGTGCTAG|TATGTTTTGA|AGTTTCTGGT|TTTTCTTTTC   960|
|TAGGTTCTTA|TAGAGACTGC|TAAGAAGCTA|GGACTCCGGT|GCCACTCAAA|GGGACAATG   1020|
|GTCACAATCG|AGGGACCTCG|TTTTAGCTCC|CGGGCAGAAA|GCTTCATGTT|CCGCACCTGG  1080|
|GGGGCGGATG|TTATCAACAT|GACCACAGTT|CCAGAGGTGT|TCTTGCTAA|GGAGGCTGGA   1140|
|ATTTGTTACG|CAAGTATCGC|CATGGGCACA|GATTATGACT|GCTGGAAGGA|GCACGAGGAA  1200|
|GCAGTAGGTG|GAATTCTTTT|CTAAGCACAT|ATAGCATGG|TTTCTGGGTG|CCAATAGGGT   1260|
|GTCTTAACTG|TTTGTTTCTA|TTACGTTAGT|TTCAGAAAGT|GCCTTTCTAC|AAGGTTTTGA  1320|
|AGTTGTTAAT|ATTTTCTGTA|GTTCCATTGG|AAGGTAAGAA|CAAAGATCAA|AAGAAAGAAA  1380|
|GAGACACTTT|TACCCAAGGA|TCAGTAGTGA|AAATAGTACA|TTGTAGGCAT|GTAGATGTGT  1440|
|TGAGAATCAT| | | | |                                                 1450|

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "sense primer"

(xi) SEQUENCE DESCRIPTION: SEQ ID NO: 24:

AATTCGGCAC GAGGCAGCAT                                                  20

(2) INFORMATION FOR SEQ ID NO: 25:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "anti-sense primer"

(xi) SEQUENCE DESCRIPTION: SEQ ID NO: 25:

TTATTTGAGC TTTGGTTCTG                                              20

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "new anti-sense primer"

(xi) SEQUENCE DESCRIPTION: SEQ ID NO: 26:

TCGGCCTCCG ACCGTAACTA                                              20

(2) INFORMATION FOR SEQ ID NO: 27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "primer for control G3PDH
            gene"

(xi) SEQUENCE DESCRIPTION: SEQ ID NO: 27:

TGGTATGGTG GAAGGACTCA TGAC                                         24

(2) INFORMATION FOR SEQ ID NO: 28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "primer for control G3PDH
            gene"

(xi) SEQUENCE DESCRIPTION: SEQ ID NO: 28:

ATGCCAGTGA GCTTCCCGTT CAGC                                         24
```